(12) United States Patent
Wallace et al.

(10) Patent No.: US 7,758,541 B2
(45) Date of Patent: Jul. 20, 2010

(54) TARGETED DRUG DELIVERY DEVICE AND METHOD

(75) Inventors: Michael P. Wallace, Fremont, CA (US); Robert J. Garabedian, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1082 days.

(21) Appl. No.: 10/920,735

(22) Filed: Aug. 17, 2004

(65) Prior Publication Data

US 2006/0041225 A1 Feb. 23, 2006

(51) Int. Cl.
*A61M 31/00* (2006.01)

(52) U.S. Cl. .................. 604/103.01; 604/96.01

(58) Field of Classification Search ............ 604/103.01, 604/103.02, 167.05, 93.01, 264, 96.01, 246, 604/248, 537
See application file for complete search history.

(56) References Cited

U.S. PATENT DOCUMENTS

| | | | |
|---|---|---|---|
| 4,515,593 A | 5/1985 | Norton | |
| 4,655,746 A | 4/1987 | Daniels et al. | |
| 4,769,005 A * | 9/1988 | Ginsburg et al. | ............ 604/264 |
| 4,904,245 A * | 2/1990 | Chen et al. | ................... 604/248 |
| 5,069,662 A | 12/1991 | Bodden | |
| 5,087,244 A | 2/1992 | Wolinsky et al. | |
| 5,207,643 A * | 5/1993 | Davis | ........................... 604/80 |
| 5,370,614 A | 12/1994 | Amundson et al. | |
| 5,380,282 A | 1/1995 | Burns | |
| 5,380,307 A | 1/1995 | Chee et al. | |
| 5,397,307 A | 3/1995 | Goodin | |
| 5,484,409 A | 1/1996 | Atkinson et al. | |
| 5,558,642 A | 9/1996 | Schweich, Jr. et al. | |
| 5,609,574 A * | 3/1997 | Kaplan et al. | ................ 604/508 |
| 5,637,086 A | 6/1997 | Ferguson et al. | |
| 5,674,192 A | 10/1997 | Sahatjian et al. | |
| 5,681,281 A * | 10/1997 | Vigil et al. | ............. 604/103.01 |
| 5,800,408 A * | 9/1998 | Strauss et al. | ................ 604/264 |
| 5,823,996 A | 10/1998 | Sparks | |
| 5,833,658 A | 11/1998 | Levy et al. | |
| 5,873,852 A * | 2/1999 | Vigil et al. | ................... 604/509 |
| 5,919,163 A | 7/1999 | Glickman | |
| 6,017,323 A | 1/2000 | Chee | |
| 6,048,332 A | 4/2000 | Duffy et al. | |
| 6,095,997 A * | 8/2000 | French et al. | ................... 604/9 |
| 6,328,720 B1 * | 12/2001 | McNally et al. | ............. 604/332 |

(Continued)

FOREIGN PATENT DOCUMENTS

EP 138634 2/2004

(Continued)

*Primary Examiner*—Nicholas D Lucchesi
*Assistant Examiner*—Christopher D Koharski
(74) *Attorney, Agent, or Firm*—Crompton, Seager & Tufte, LLC

(57) ABSTRACT

A targeted drug delivery device is provided. The device comprises an elongated member with proximal and distal ends, a plurality of infusion ports associated with the distal end of the elongated member, and a selector mechanism for selectively placing an introducer port into fluid communication with at least one infusion port. A method for treating tissue is also provided. The method comprises introducing a medical device into the tissue, selecting an region of the tissue to treat, positioning the medical device in proximity to the region, and introducing a medicament through the device to treat only that region.

20 Claims, 20 Drawing Sheets

U.S. PATENT DOCUMENTS

| | | |
|---|---|---|
| 6,378,218 B2 | 4/2002 | Sigwart et al. |
| 6,413,203 B1 | 7/2002 | Sahatjian |
| 6,575,932 B1 | 6/2003 | O'Brien et al. |
| 6,602,241 B2 | 8/2003 | Makower et al. |
| 6,616,626 B2 | 9/2003 | Crank et al. |
| 6,623,452 B2 | 9/2003 | Chien et al. |
| 6,635,027 B1 | 10/2003 | Cragg et al. |
| 6,638,245 B2 | 10/2003 | Miller et al. |
| 6,656,152 B2 | 12/2003 | Putz |
| 6,685,648 B2 | 2/2004 | Flaherty et al. |
| 6,692,458 B2 | 2/2004 | Forman et al. |
| 2002/0077594 A1 | 6/2002 | Chien et al. |
| 2003/0130572 A1 | 7/2003 | Phan et al. |
| 2004/0064094 A1 | 4/2004 | Freyman |

FOREIGN PATENT DOCUMENTS

| | | |
|---|---|---|
| GB | 2269538 | 2/1994 |
| WO | WO 00/40281 | 7/2000 |
| WO | WO 00/67825 | 11/2000 |

\* cited by examiner

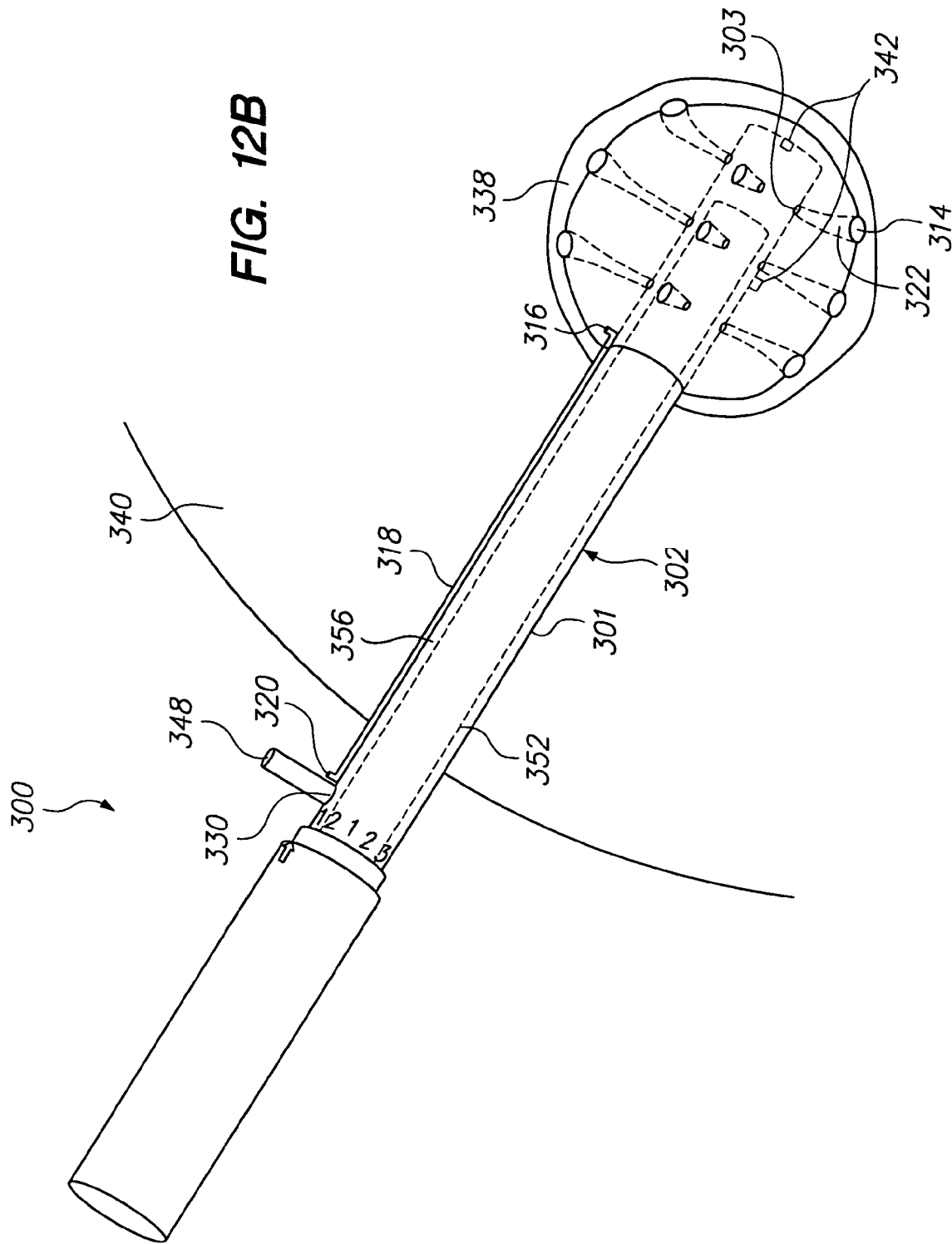

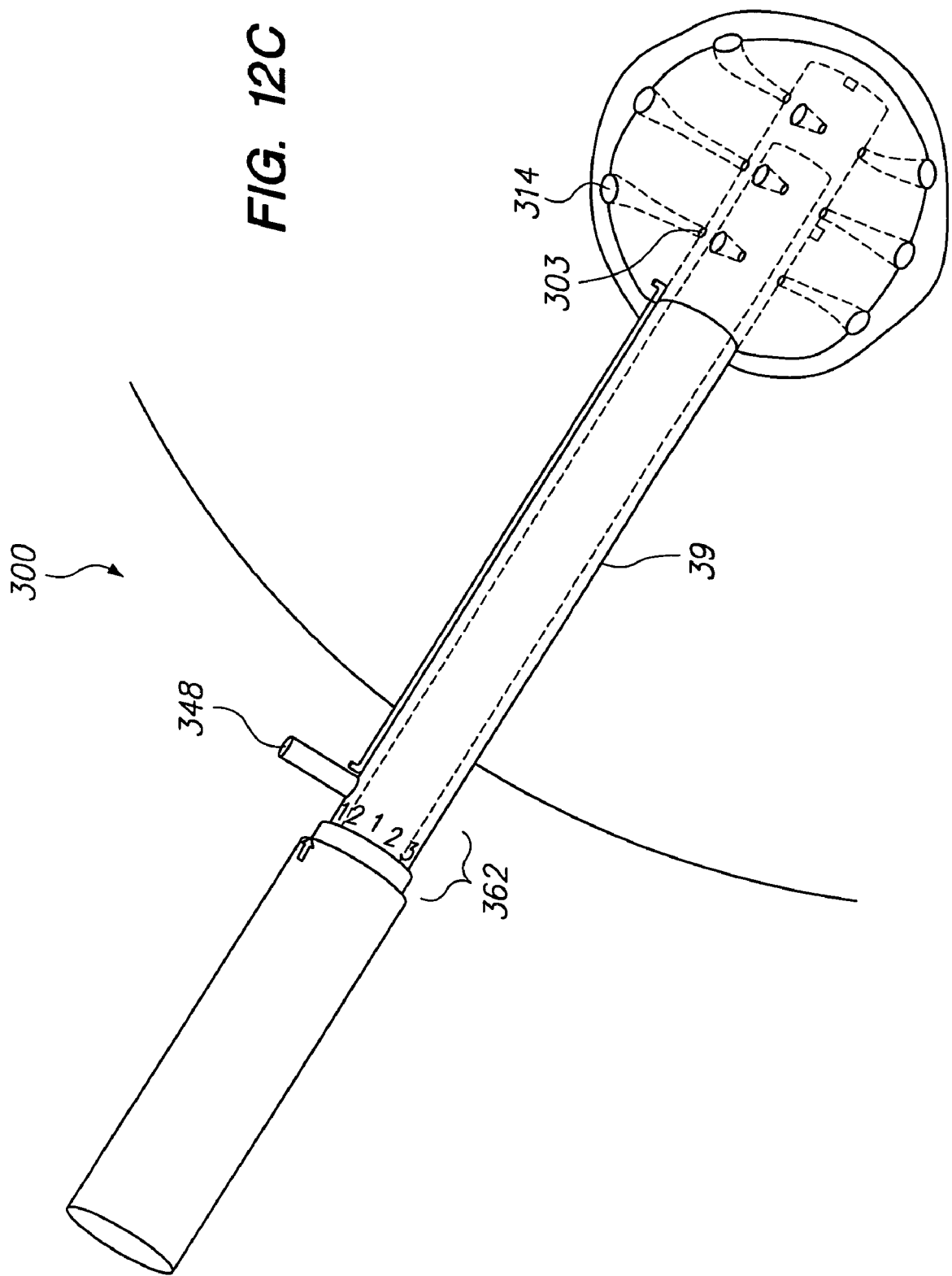

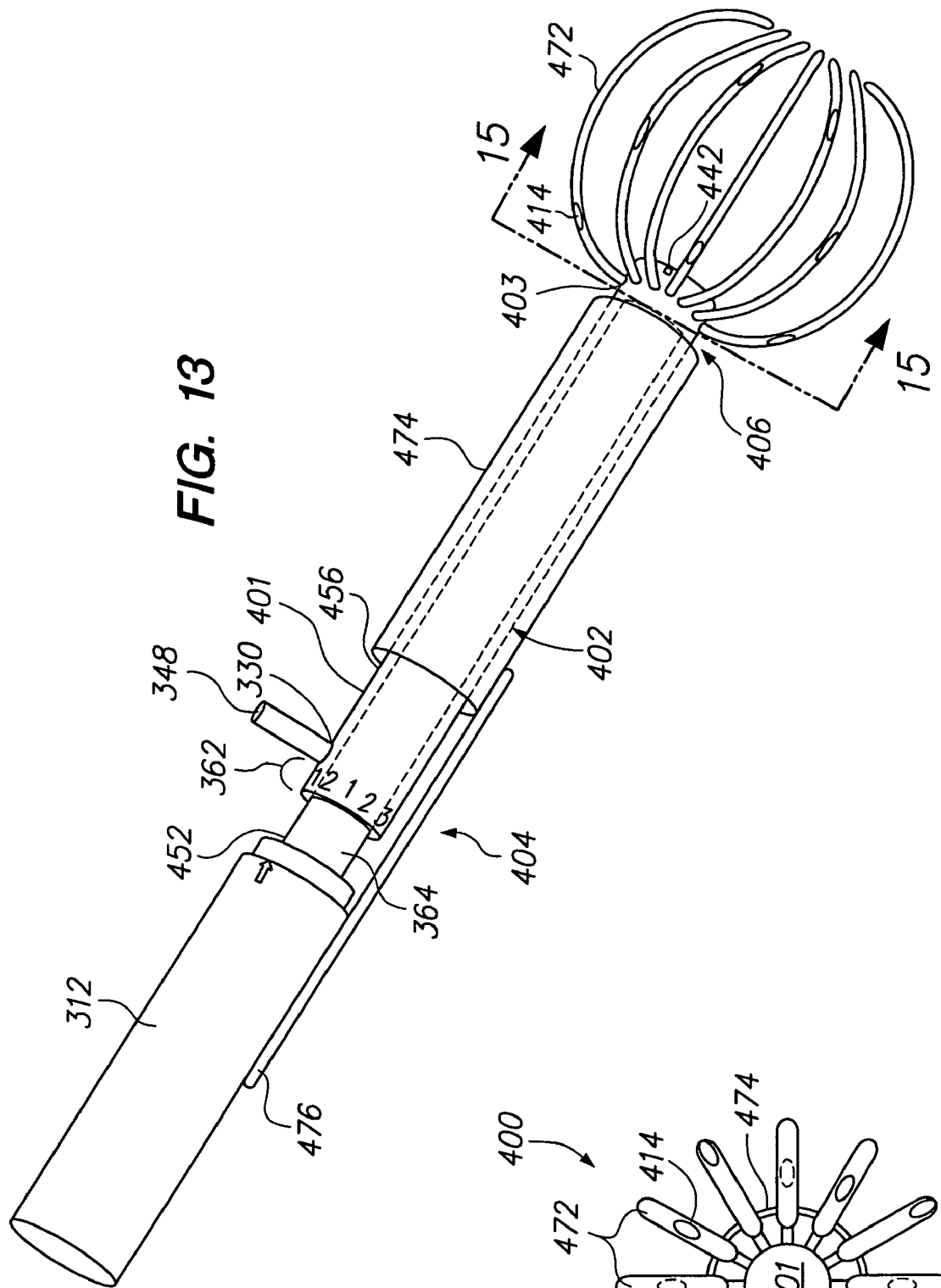
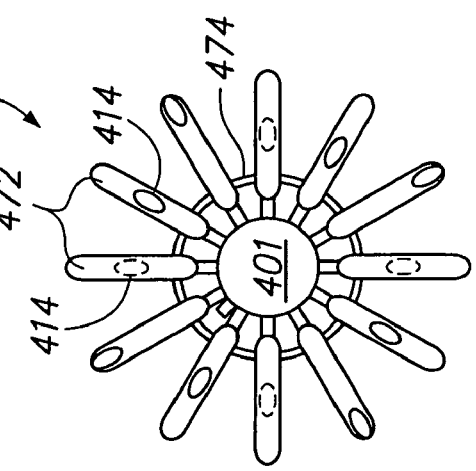

TARGETED DRUG DELIVERY DEVICE AND METHOD

FIELD OF THE INVENTION

The invention relates to medical devices and methods for delivering fluids into a patient's body, and in particular, to devices and methods for delivering a medicament into a lesion.

BACKGROUND OF THE INVENTION

Many medical procedures require treating deep tissues using liquid therapeutic agents. For instance, liquid chemotherapeutic agents are often used to treat interstitial spaces from which tumors have been surgically excised.

The theory behind the chemotherapeutic treatment of these excised interstitial spaces is that even a single malignant cell left in the margins of an excised interstitial space can multiply into a new tumor. Therefore the excised interstitial space is treated with toxic chemotherapeutic agents to destroy any remaining malignant cells. Removing tumors from deep within the body, along with a margin of healthy tissue, leaves a substantial space to be treated. The fluid chemotherapeutic agent is often delivered into the space via a catheter. However, due to the extreme toxicity of chemotherapeutic agents and variability in the size of the margin, chemotherapeutic treatment of an excised interstitial space will lead to the destruction of many healthy, and sometimes critical, cells.

The inability to direct chemotherapy agents to specific parts of an excised interstitial space presents several problems for chemotherapy treatment. Due to the large size of the interstitial space relative to areas requiring treatment, it is difficult to obtain predictive infusion of a drug. Also, filling an excised interstitial space results in the use of an excess quantity of the chemotherapeutic agent, which increases the cost of treatment. Increasing the dose of chemotherapeutic agent also increases the amount of the agent absorbed into a patient's system, making it difficult to achieve a therapeutic concentration of a drug locally at a target site within the excised interstitial space without producing unwanted systemic side effects.

Although many drugs are known for the treatment of various diseases of deep tissues, current techniques for delivering those drugs cannot target specific sites within an excised interstitial space. Often, a greater than needed dose of a drug is used and unintended tissue is exposed to the drug. Lack of targeted delivery impacts both the efficacy and economy of these various treatments.

There, thus, remains a need to provide improved methods for delivering fluids to specific deep tissue targets in a more targeted manner.

SUMMARY OF THE INVENTION

In accordance with a first aspect of the present inventions, a medical device is provided. The medical device comprises an elongated member, which in one embodiment is rigid to facilitate its percutaneous introduction into the patient's body. In alternative embodiments, the member may be semi-rigid or even flexible. The medical device further comprises a plurality of infusion ports, which may be associated with the distal end of the elongated member in any one of a variety of manners.

For example, the ports may be formed into the distal end of the member itself. In this case, the member may comprise a bendable distal section, and the medical device may further comprise an actuator configured for bending the distal end of the elongated member into an arc. The actuator can be, e.g., a tension cord attached to the distal end of the elongated member. Alternatively, the medical device may have a radially expandable body surrounding the distal end of the member, in which case, the infusions ports may be formed onto the expandable body. In one embodiment, the expandable body is a balloon, in which case, the medical device may comprise an inflation duct extending along the member in fluid communication with the interior of the balloon. In this manner, the balloon may be selectively inflated by introducing inflation medium into the inflation duct, and deflated by removing inflation medium from the inflation duct. In another embodiment, the expandable body comprises a plurality of resilient arms that radially bend outward in the absence of a radially compressive force, in which case, the medical device may comprise a sheath axially slidable along the member and configured for applying a radially compressive force to the plurality of arms. In this manner, the resilient arms can be selectively collapsed by sliding the sheath over the arms, and expanded by sliding the sheath off of the arms.

The medical device further comprises a selector mechanism configured for selectively placing the introduction port into fluid communication with at least one infusion port. In one embodiment, the selector mechanism is configured for selectively placing the introduction port into fluid communication with a single infusion port. In alternatively embodiments, the selector mechanism can be configured for selectively placing the introduction port into fluid communication with multiple infusion ports.

In the preferred embodiment, the medical device comprises a plurality of fluid delivery channels in fluid communication with the respective infusion ports. The channels may have proximal openings that either terminate at the proximal end of the member or at the distal end of the member, and may be, e.g., axially disposed or radially disposed.

If the proximal openings of the channels are axially disposed, one embodiment of the selector mechanism may comprise a rotatable selector plate with at least one through-hole that can be selectively aligned with a proximal opening of a channel, thereby allowing selection of a delivery channel and corresponding infusion port. In this case, the selector mechanism may further comprise a manifold with a cavity in fluid communication between the introduction port and the at least one selector plate hole. A flush port may optionally be in fluid communication with the manifold cavity.

If the proximal openings of the channels are radially disposed, one embodiment of the selector mechanism may comprise a rod extending through the member and at least one annular arrangement having a gap that can be aligned with a proximal opening of a channel. The annular arrangement can be, e.g., a plurality of radially extending, evenly distributed, stops, in which case, the gap represents a missing stop. Alternatively, the annular arrangement can be a cam, in which case, the gap is formed in the cam. An annular lumen can be formed between the rod and the member to provide fluid communication between the introduction port and the channels.

In accordance with a second aspect of the present inventions, a method of treating a lesion located remotely in tissue, e.g., brain tissue, is provided. The method comprises introducing a medical device having a plurality of ports into the tissue adjacent the lesion. The medical device can be, e.g., the previously described medical device, or alternatively, can be another type of medical device with multiple ports. In one method, the lesion is a tumor, in which case, the tumor is preferably removed to create an interstitial space in which the medical device is introduced. The method further comprises selecting a region of the lesion to treat, and then selecting at least one of the ports on the medical device. If the previously described medical device is used, the selector mechanism can be operated to place the introducer port into fluid communication with the selected port(s).

The method further comprises introducing a medicament (such as, e.g., a chemotherapeutic agent) into the introducer port, which will then be delivered to the tissue via the selected port(s). In one method, the medicament is delivered by forced convection, so that it is more easily absorbed into the tissue. Optionally, another region of the lesion can be treated, in which case, at least another port can be selected in the same manner previously described. A medicament (which may be the same as or different from the first medicament) can then, again, be introduced into the introducer port, which will then be delivered to the tissue via the other selected port(s).

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIGS. 12A to 12C are perspective views of a method of using the delivery device of FIG. 9 to deliver medicament to an interstitial space within tissue;

FIG. 13 is an exploded perspective view of a targeted drug delivery device constructed in accordance with yet another preferred embodiment of the present invention;

FIG. 14 is a distal axial view of the delivery device of FIG. 13;

DETAILED DESCRIPTION OF THE PREFERRED EMBODIMENTS

Figure 1:
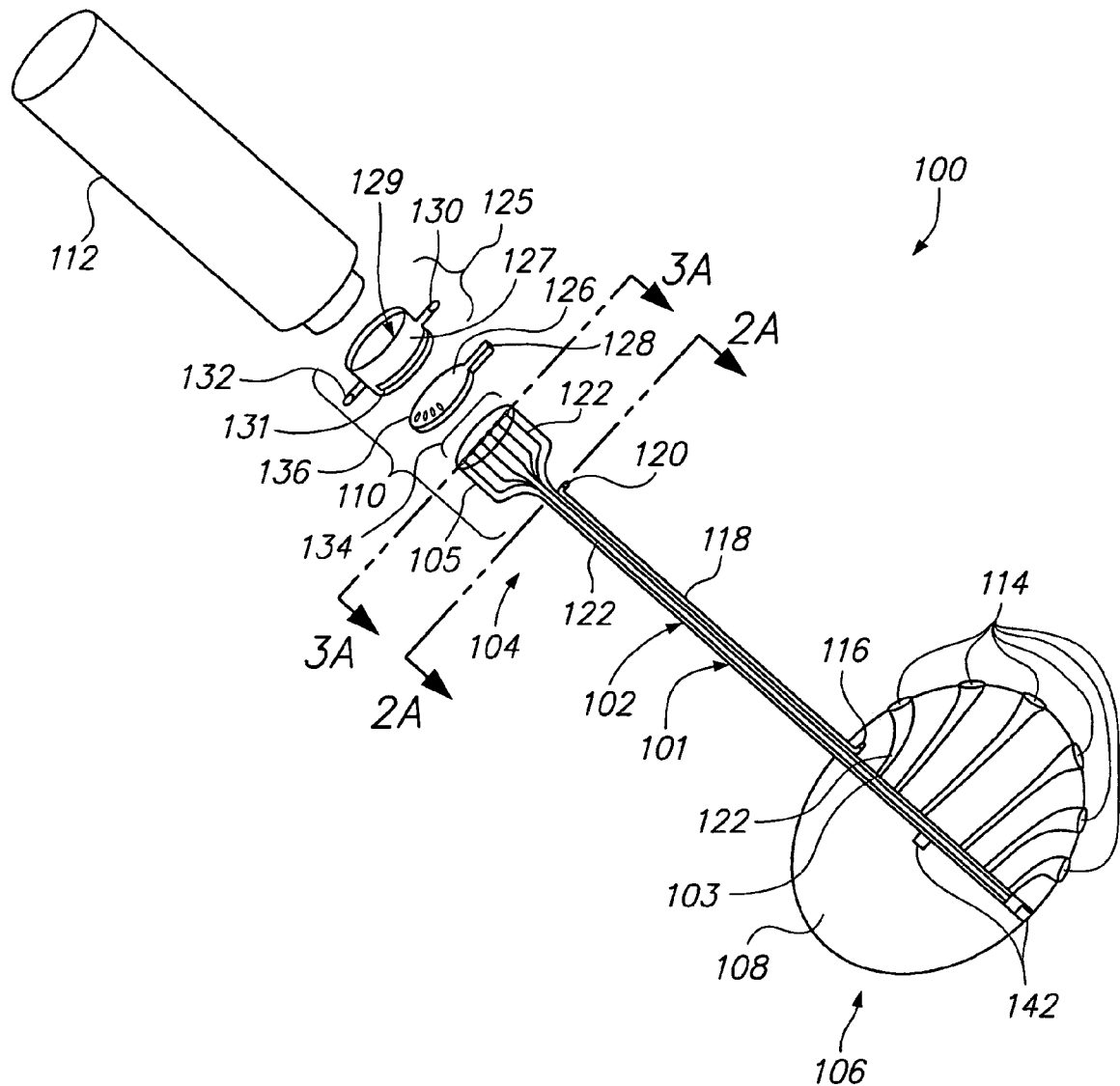
FIG. 1 is an exploded perspective view of a targeted drug delivery device constructed in accordance with a preferred embodiment of the present invention.

Referring to FIG. 1, a preferred embodiment of a targeted drug delivery device 100 will now be described. The delivery device 100 generally comprises an elongated delivery member 102 having a proximal end 104 and a distal end 106, an expandable body, and specifically a balloon 108, mounted along the distal end 106 of the delivery member 102 for delivery of drugs to a selected site, a drug port selector assembly 110 mounted to the proximal end 104 of the delivery member 102, and a handle 112 mounted to the proximal end of the selector assembly 110.

The delivery member 102 comprises an elongated tube 101 that may be formed using a standard extrusion process. In the preferred embodiment, the elongated tube 101 is rigid or semi-rigid, but may be flexible in some circumstances. The elongated tube 101 may be formed from any biocompatible material, including plastic and other suitably rigid polymers. The elongated tube 101 has a series of holes 103 formed into its distal end during extrusion. The delivery member 102 comprises an inflation duct 118 that extends along the elongated tube 101. In the illustrated embodiment, the inflation duct 118 takes the form of a separate tube of extruded polymer that is laminated to the outside of the elongated tube 101. Alternatively, the inflation duct 118 can take the form of a separate tube or an integrated lumen that extends within the interior of the elongated tube 101. The inflation duct 118 defines a proximal opening 120, which connects to a source of inflation medium, such as a syringe, and a distal opening 116, which terminates within the interior of the balloon 108. Thus, it can be appreciated that fluid introduced into the proximal opening 120 of the inflation duct 118 will travel through the distal opening 116 of the inflation duct 118 and into the balloon 108, thereby placing the balloon 108 into its expanded geometry (as shown in FIG. 1). Fluid removed from the proximal opening 120 of the inflation duct 118 will, in turn, remove the fluid from the balloon 108, thereby placing the balloon 108 into its collapsed geometry (shown in FIG. 5A).

The delivery member 102 further comprises drug delivery lumens 122 that extend along the elongated tube 101, out the holes 103 at the distal end 106 of the elongated tube 101 and into the interior of the balloon 108. In the illustrated embodiment, the drug delivery lumens 122 are formed of separate tubes extruded from polymer. The delivery member 102 further comprises a plurality of locating markers 142, which may be radio-opaque markers, signal transmitters, or signal receivers, mounted to the distal end of the elongated tube 101. The markers 142 interact with navigational systems (not shown) to more precisely position the delivery device 100. Also, a cutting edge (not shown) may be formed or separately attached to the distal end of the elongated tube 101. A skilled artisan will appreciate that a variety of cutting devices and catheter geometries and shapes would permit puncturing through overlying tissue.

The balloon 108 preferably comprises a highly compliant material that elastically expands upon pressurization. Because the balloon 108 elastically expands from the deflated state to the inflated state, the balloon 108 has a low profile in the deflated state and does not require balloon folding as with other non-compliant or semi-compliant balloon materials. Preferably, the balloon 108 is blow molded from a silicone. It should be noted, however, that non-compliant or semi-compliant balloon materials can be used without straying from the principles of the invention. The balloon 108 has a diameter of 15 mm to 20 mm.

The balloon 108 defines a plurality of drug infusion ports 114 on its surface. The ports 114 may either be formed into the balloon 108 during molding, or they are formed into the balloon 108 with a laser. The distal ends of the drug delivery lumens 122, which extend into the interior of the balloon 108 via the holes 103 within the distal end of the elongated tube 101, are connected to the ports 114 by heat bonding or with an adhesive. Because the ports 114 are positioned on the balloon 108, the size of the ports 114 increases as the balloon 108 is inflated. The size of the ports 114 may be selected to allow the balloon 108 to control the pressure of the fluid to be introduced through the ports 114. The number of the ports 114 may be selected to adjust the precision with which a location on the balloon 108 will be selected. In this preferred embodiment, the ports 114 are equally spaced along a line parallel to the longitudinal axis of the delivery member 102. The ports 114 may extend at an orthogonal angle through the wall of the balloon 108, or at a non-orthogonal to project the fluid more distally or more proximally as desired. Alternatively, protrusions (not shown) may be formed on the balloon 108 during blow molding and the ports 114 may be positioned on these protrusions. Protrusions will allow the balloon 108 to more easily grasp overlying tissue when the balloon 108 is inflated for more directed delivery of a drug.

In the illustrated embodiment, the balloon 108 is chemically bonded to the distal end of the elongated tube 101 with an adhesive, or the two elements can be heat bonded together. During bonding, the holes 103 in the elongated tube 101 should be sealed around the drug delivery lumens 122, so that the interior of the elongated tube 101 is not in fluid communication with the interior of the balloon 108.

Figure 2A:
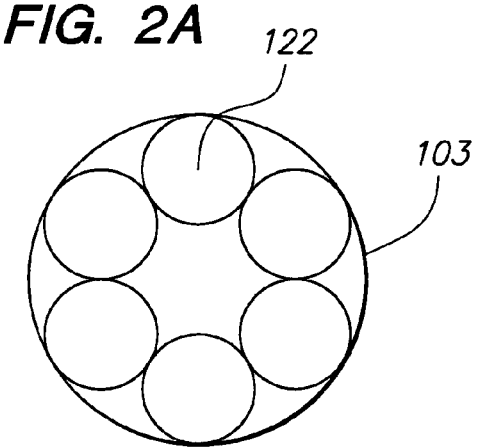
FIG. 2A is a proximal cross sectional view of a delivery member used in the delivery device of FIG. 1, taken along line 2A-2A in FIG. 1.
Figure 2B:
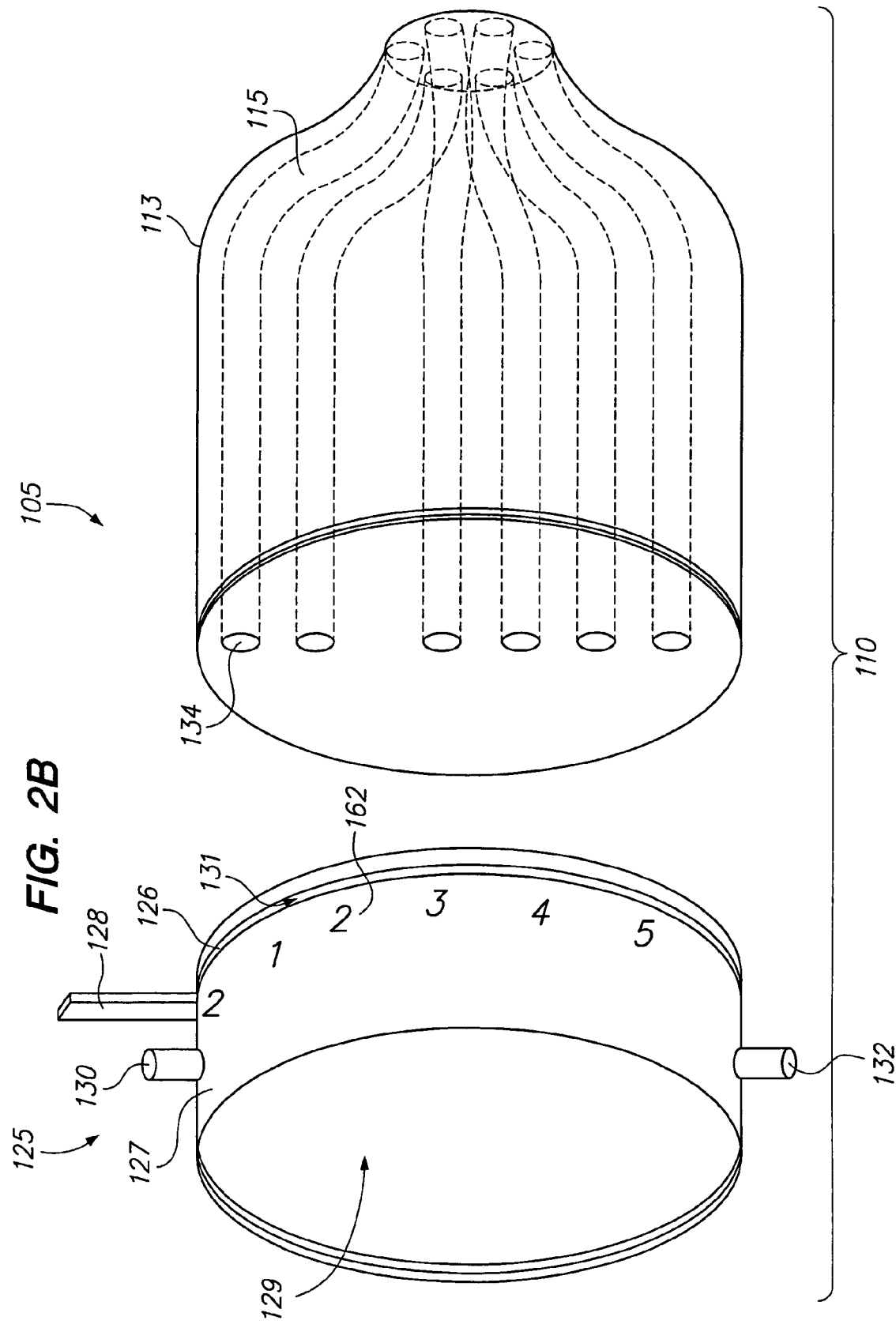
FIG. 2B is a perspective view of a selector mechanism used in the delivery device of FIG. 1.

Referring to FIG. 2B, the selector assembly 110 comprises an adapter 105 that provides a means for more accessing the proximal ends of the drug deliver lumens 122, a manifold 125 that provides a means for introducing different drugs into the delivery member 102, and a selector plate 126 that provides a means for selecting a specific drug delivery lumen 122, and thus a specific drug infusion port 114, through which the introduced drug will be delivered.

In particular, the adapter 105 comprises an adaptor housing 113 and a plurality of adapter lumens 115 that extend through the adaptor housing 113. The adaptor housing 113 may be formed using an extrusion process and may be composed of a suitably rigid material, such as polymer, and is mounted to the proximal end of the elongated tube 101 using suitable means, such as heat or chemical bonding. In the illustrated embodiment, the adapter lumens 115 are formed within the adaptor housing 113 during the extrusion process. The distal ends of the adapter lumens 115 are in fluid communication with the respective drug delivery lumens 122. For example, the proximal ends of the drug delivery lumens 122 can be suitably bonded within openings at the distal ends of the adapter lumens 115. The proximal ends of the adapter lumens 115 are arranged in a single line of drug channel openings 134, the function of which will be described in detail below. Thus, it can be appreciated that the adapter 105 allows the tightly spaced drug delivery lumens 122 (shown in FIG. 2) to be more easily accessed. For the purposes of this specification, the combination of each drug delivery lumen 122 and respective adapter lumen 115 combine to form a drug delivery channel that proximally terminates at a drug channel opening 134 and distally terminates in a drug infusion port 114. Of course, a drug delivery channel can be formed of a single lumen or more lumens connected to each other, depending upon the construction of the device.

The manifold 125 comprises a ring-shaped structure 127, which defines an open manifold cavity 129, a slot 131, and a drug inlet port 130 and flush port 132 in fluid communication with the manifold cavity 129. The selector plate 126 comprises a plurality of selector through-holes 136 and is rotatably mounted in the slot 131 with rubber gaskets (not shown) on either side of the selector plate 126 to secure the selector assembly 110 against leaks. The selector plate 126 is mounted such that the drug inlet port 130 can only communicate with the drug channel openings 134 through the selector holes 136.

Figure 3A:
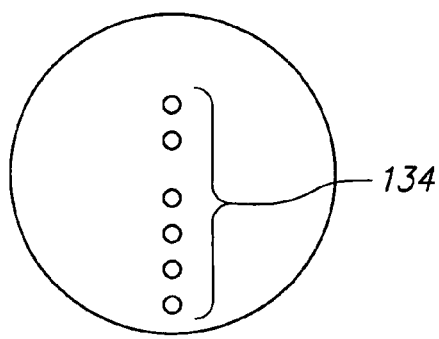
FIG. 3A is a cross-sectional view of an adaptor used in the delivery device of FIG. 1, taken along line 3A-3A in FIG. 1.
Figure 3B:
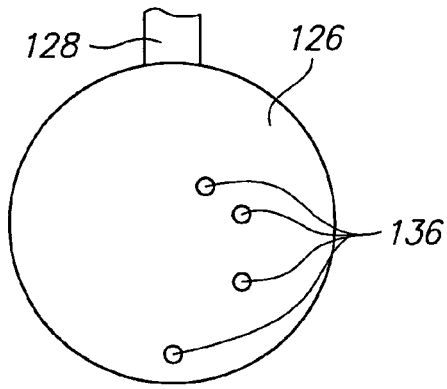
FIG. 3B is a proximal axial view of a selector plate used in the delivery device of FIG. 1.

The selector holes 136 align with a specific channel opening 134 when the selector plate 126 is rotated to the proper position. In particular, the selector holes 136 are positioned, so that when the selector plate 126 is rotated, at most one of the channel openings 134 is open (i.e., one of the selector holes 136 is in communication with the channel opening 134), while the other channel openings 134 are blocked by the selector plate 126 (i.e., none of these selector holes 136 are in communication with the other channel openings 134). In the illustrated embodiment, this is accomplished by arranging the openings 134 of the lumens 122 in a straight line, as best shown in FIG. 3A, and arranging the holes 136 in the selector plate 126 in an arc, as best shown in FIG. 3B. The selector plate 126 comprises a clutch 128, which allows a user to more easily rotate the selector plate 126 to the selected position, as well as determine the position of the selector plate 126. The elongated delivery member 102 comprises key information 162, which interacts with the clutch 128 to indicate the position of the selector plate 126.

The handle 112 is connected to the selector assembly 110 using, e.g., a threaded arrangement. The handle 112 can be ergonomically designed for ease of operation of the delivery device 100.

Figure 4A:
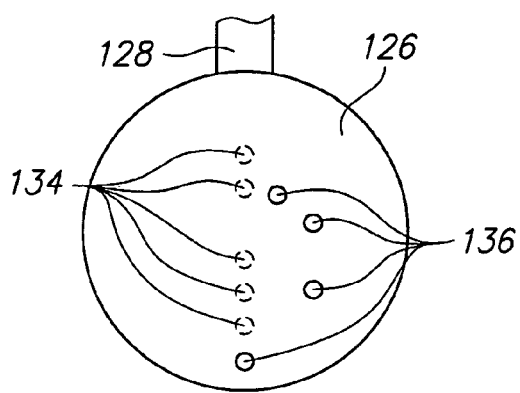
FIGS. 4A to 4G are proximal axial views of the selector plate used in the delivery device of FIG. 1, showing different positions of the selector plate for opening and closing channel openings.

Referring to FIGS. 4A to 4G, the operation of the selector plate 126, in determining the drug channel opening 134, and thus the corresponding drug infusion port 114 (see FIG. 1), through which fluid will be introduced is described. In FIGS. 4A to 4G, the relationship between rotation of the selector plate 126 and the alignment of selector holes 136 with the channel openings 134 (shown in phantom) can be seen. When the selector plate 126 is oriented to the North (12 o'clock position), as shown in FIG. 4A, only the lowest channel opening 134 is aligned with a selector hole 136, and thus open. Thus, the drug inlet port 130 will be in fluid communication with the corresponding drug infusion port 114. The other channel openings 134 are closed off by the selector plate 126, and thus, the drug inlet port 130 will not be in fluid communication with the remaining infusion ports 114.

Figure 4B:
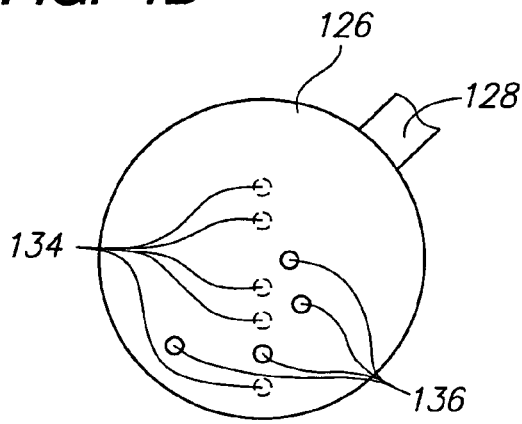
Figure 4C:
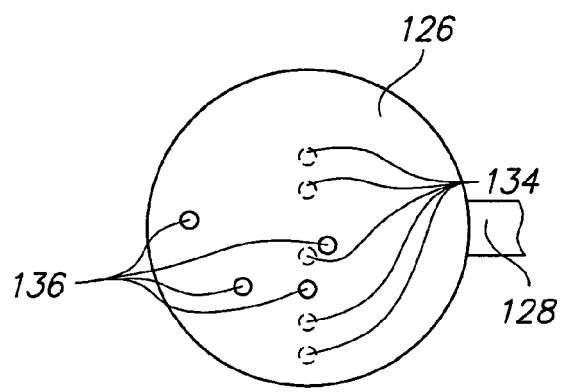
Figure 4D:
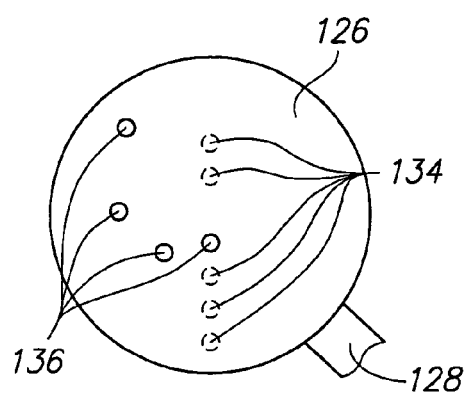
Figure 4E:
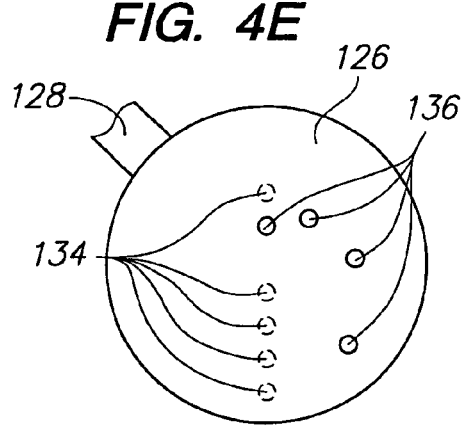
Figure 4F:
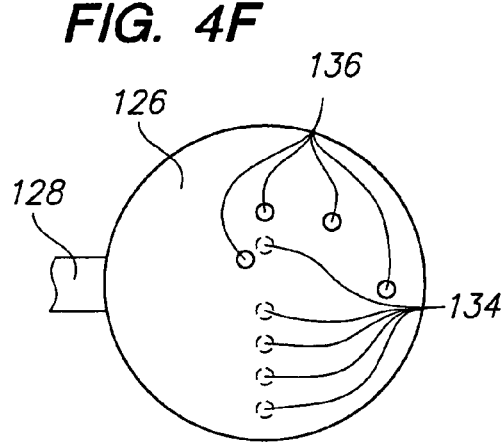
Figure 4G:
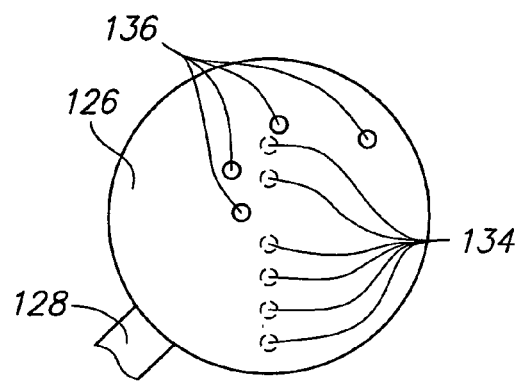

When the clutch 128 is oriented to the North-East (1:30 o'clock position), as shown in FIG. 4B, only the second lowest channel opening 134 is aligned with a selector hole 136, and thus open. When the clutch 128 is oriented to the East (3 o'clock position), as shown in FIG. 4C, only the third lowest channel opening 134 is aligned with a selector hole 136, and thus open. When the clutch 128 is oriented to the South-East (4:30 o'clock position), as shown in FIG. 4D, only the third highest channel opening 134 is aligned with a selector hole 136, and thus open. When the clutch 128 is oriented the North-West (10:30 o'clock position), as shown in FIG. 4E, only the second highest channel opening 134 is aligned with a selector hole 136, and thus open. When the clutch 128 is oriented to the West (9 o'clock position), as shown in FIG. 4F, only the highest channel opening 134 is aligned with a selector hole 136, and thus open. When the clutch is oriented to the South-West (7:30 o'clock position), as shown in FIG. 4G, no channel openings 134 are aligned with a selector hole 136, and thus all channel openings 134 are closed. As will be described in further detail below, this last orientation is useful, e.g., in order to flush any drug remaining in the manifold cavity 129.

Alternatively, other types of selector plates with different through-hole configurations can be incorporated into the selector mechanism to allow multiple lumens 122 to be opened simultaneously.

Figure 5A:
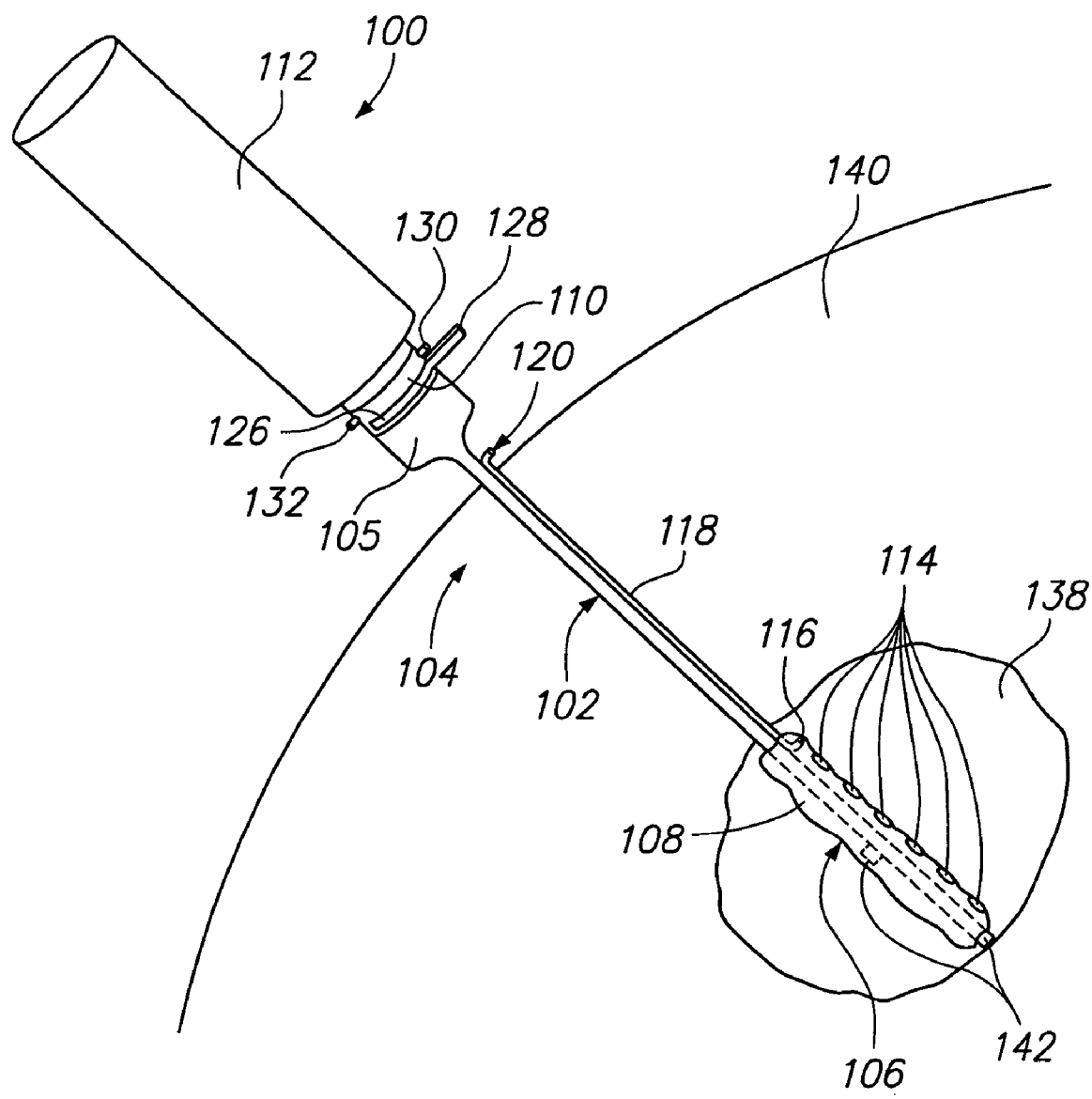
FIGS. 5A to 5C are perspective views of a method of using the delivery device of FIG. 1 to deliver medicament to an interstitial space within tissue.
Figure 5B:
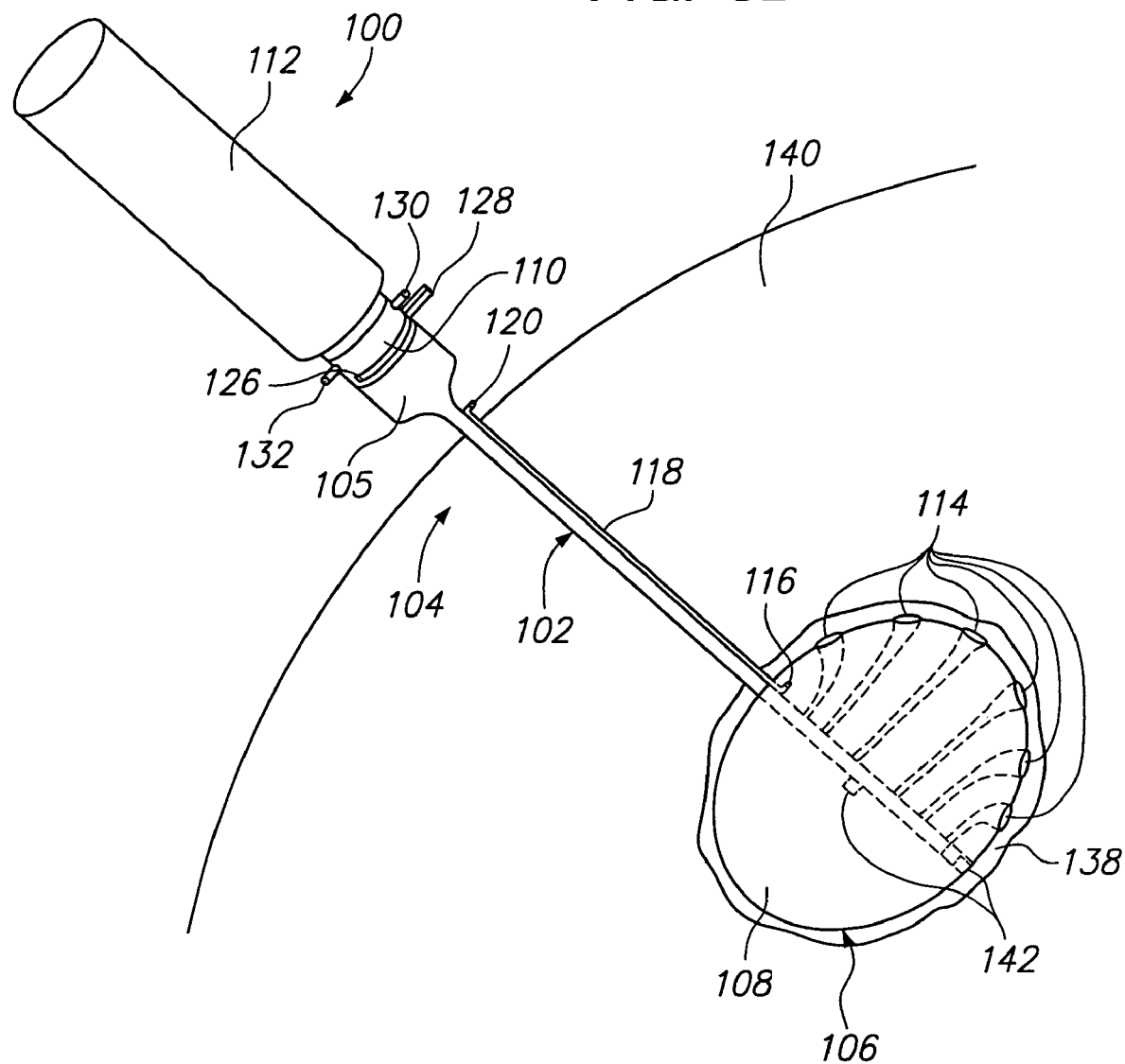
Figure 5C:
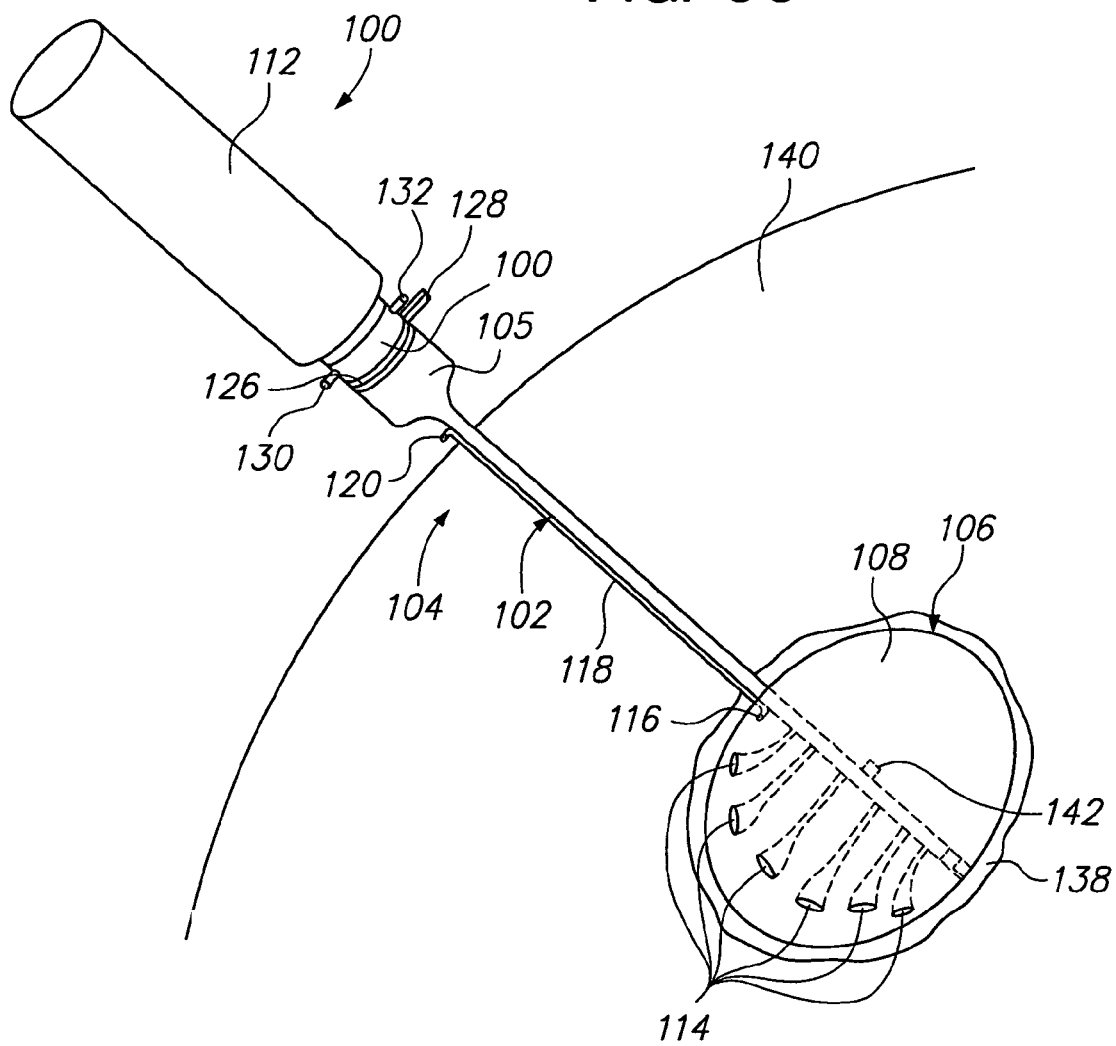

Referring now to FIGS. 5A to 5C, the operation of the delivery device 100 in treating an interstitial space 138 with a medicament from which a tumor (not shown) has been excised will now be described. The medicament used to treat the tissues can be chemotherapeutic agent. Useful chemotherapeutic agents can include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

First, the delivery device 100 is inserted through the overlying tissue 140 and into the interstitial space 138 until the distal tip of the delivery member 102 reaches the distal end of the interstitial space 138 (FIG. 5A). The markers 142 can be used to more precisely position the delivery device 100.

An inflation medium is then introduced into the inflation port 120, through the inflation duct 118, and into the balloon 108, thereby expanding the balloon 108 until all of its surfaces are juxtaposed to the interior margin of the interstitial space 138 (FIG. 5B). Because the balloon 108 is compliant, it will conform to the margin of the interstitial space 138, thereby placing the balloon 108 into uniform contact with the margin and minimizing the potential of damage to healthy tissue due to over expansion of the balloon 108. The balloon 108 may optionally be expanded by filling it with a coolant, thereby reducing the temperature of the overlying tissue 140 and further minimizing blood loss.

The delivery device 100 is then rotated about its longitudinal axis to position the line of infusion ports 114 along the tissue to be treated. If necessary, the balloon 108 can be partially deflated by releasing fluid from the inflation port 120 to facilitate rotation of the balloon. The clutch 128 is manipulated to rotate the selector plate 126 to select, as described above, the drug delivery lumen 122, and thus, the drug infusion port 114, through which drug will be delivered. The markers 142 can be used to more precisely identify the rotation of the delivery device 100.

Figure 6A:
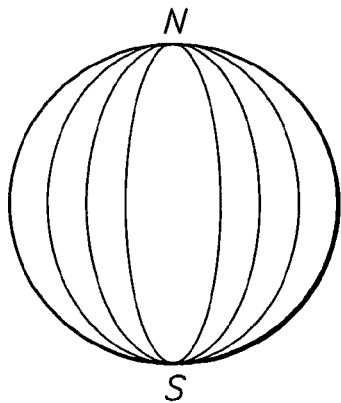
FIGS. 6A and 6B are perspective views of expandable body of the delivery device of FIG. 1, as represented by a globe, including lines of longitude and latitude, respectively.
Figure 6B:
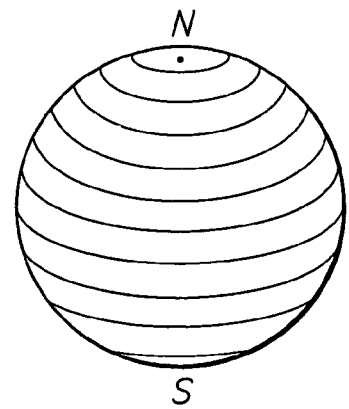

Imagining the balloon 108 as a spherical globe with the distal tip of the delivery device 100 at the North pole helps to conceptualize the coordinate system used to target drug delivery. Rotating the delivery device 100 selects a line of longitude as depicted in FIG. 6A. Rotating the selector plate 126 to one of the orientations shown in FIGS. 4A-4E selects a port 114, and therefore a line of latitude, as depicted in FIG. 6B. With both longitude and latitude determined, a specific region on the margin of interstitial space 138 where the drug is to be delivered, has been selected.

Once the region on the margin of the interstitial space has been selected for treatment, a medicament is delivered into the drug inlet port 130 while the flush port 132 is closed. The medicament will travel into the manifold cavity 129, through the selector hole 136 in the selector plate 126, into the open lumen 122 via the channel opening 134, and out the corresponding infusion port 114. The proximity of the selected infusion port 114 to the selected region on the margin of the interstitial space 138 will result in forced convection delivery of the medicament to the tissue 140.

The delivery device 100 can optionally be flushed with a biologically inactive liquid, such as saline or Ringer's solution, to ensure that all of the medicament has been delivered to the region. If flushing the interstitial space 138 with additional liquid is not desirable, the excess volume represented by the manifold cavity 129 and the drug delivery lumen 122 can be taken into account when calculating the amount of the medicament to be used.

If a second region on the margin of the interstitial space 138 is to be treated, the balloon 108 can be rotated to select a line of longitude and/or the selector plate 126 can be rotated to select a line of latitude (see FIG. 5C). If the second region is to be treated with the same medicament as the first region, the medicament is again delivered through the drug inlet port 130. Additional regions can be treated with the same medicament in the same manner.

If the second or subsequent regions are to be treated with a different medicament, however, the medical device 100 is preferably flushed to remove any traces of the first medicament from the medical device 100. In particular, the selector plate 126 is rotated until all channel openings 134 are closed (see FIG. 4G) and any medicament remaining in the manifold cavity 129 is flushed out of the flush port 132 by opening the flush port 132 and flushing manifold cavity 129 with air or a biologically inactive liquid introduced through the introducer port 130.

Once all selected points on the margin of the interstitial space 138 have been treated, the balloon 108 can be deflated by removing the inflation medium from the proximal opening 120, thereby placing the balloon 108 in its deflated state. The delivery device 100, in its low profile state (see FIG. 5A), can then be removed from the tissue 140.

Figure 7:
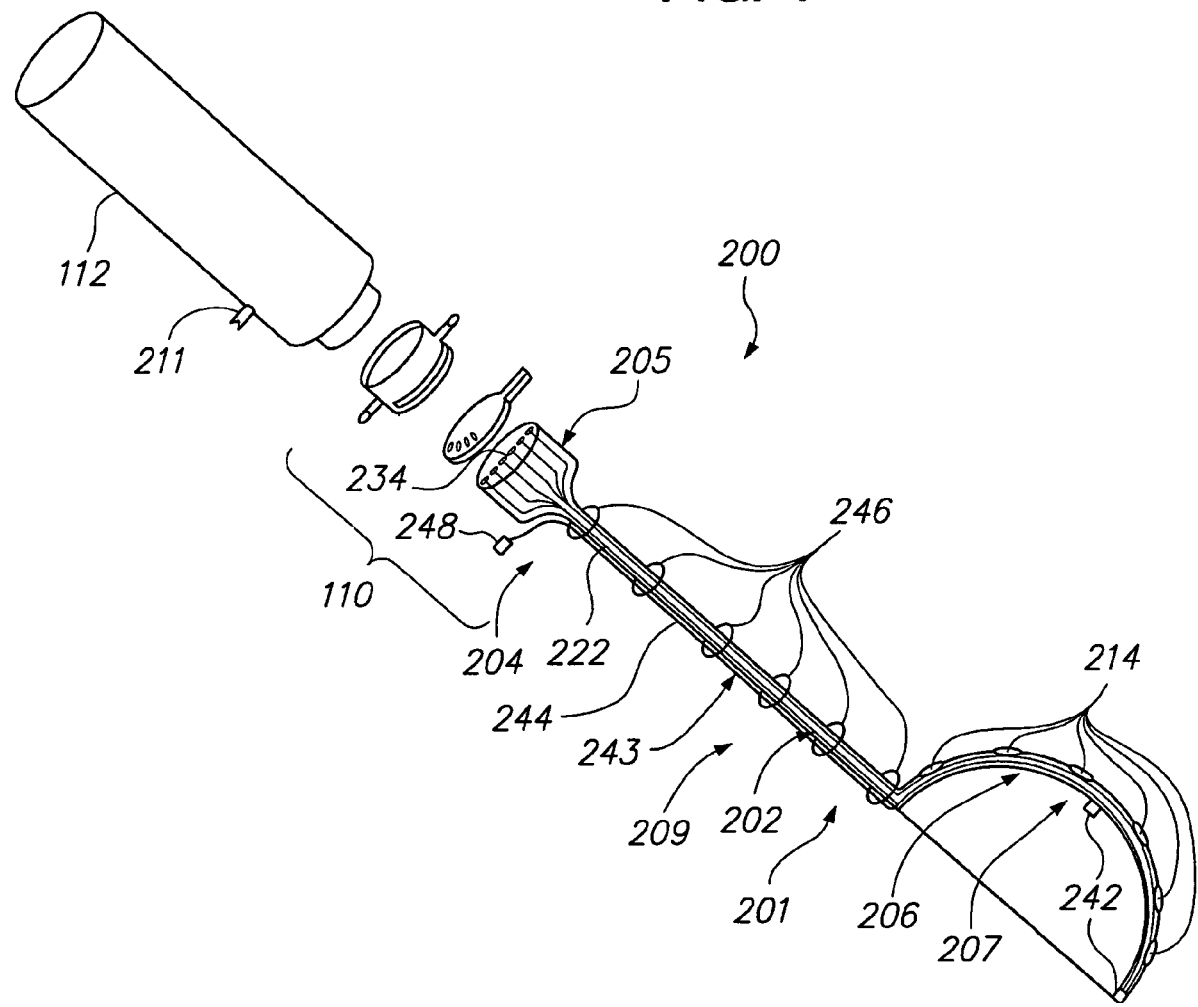
FIG. 7 is an exploded perspective view of a targeted drug delivery device constructed in accordance with another preferred embodiment of the present invention.

Referring now to FIG. 7, another preferred embodiment of a targeted drug delivery device 200 will now be described. The delivery device 200 generally comprises an elongated delivery member 202 having a proximal end 204 and a distal end 206, a tensioning assembly 243 mounted along the delivery member 202, and the previously described selector assembly 110 and handle 112.

Like the previously described delivery member 102, the delivery member 202 comprises an elongated tube 201 and drug delivery lumens 222 that extend through the tube 201 between the proximal 206 and distal ends 204. The distal ends of the drug delivery lumens 222, however, terminate in drug infusion ports 214 that extend along one lateral side of the elongated tube 201 at the distal end 206.

The elongated tube 201 has a distal bendable section 207, which is composed of an easily flexible deformable, yet resilient, material, such as nickel titanium or polyimide, and a proximal rigid section 209, which is composed of a more rigid material, such as plastic or other suitably rigid polymers. In this manner, the distal bendable section 207 will be more apt to bend into an arc under tension (as illustrated in FIG. 7), than would the proximal section. The resiliency of the distal bendable section 207 also allows it to bend back into a rectilinear geometry once the tension is removed. To ensure that the bendable section 207 bends in a manner that consistently places the infusion ports 214 on the outside of the arc, one lateral side of the distal bendable section 207 (in this case, the lateral side on which the infusion ports 214 are disposed) can be composed of a more flexible material than that of the opposite lateral side. Alternatively, a discrete resilient flat member (not shown) can be formed within one lateral side of the distal bendable section 207 to provide the desired bending characteristics. The delivery member 202 can carry markers 242 to provide navigational ability.

Figure 8A:
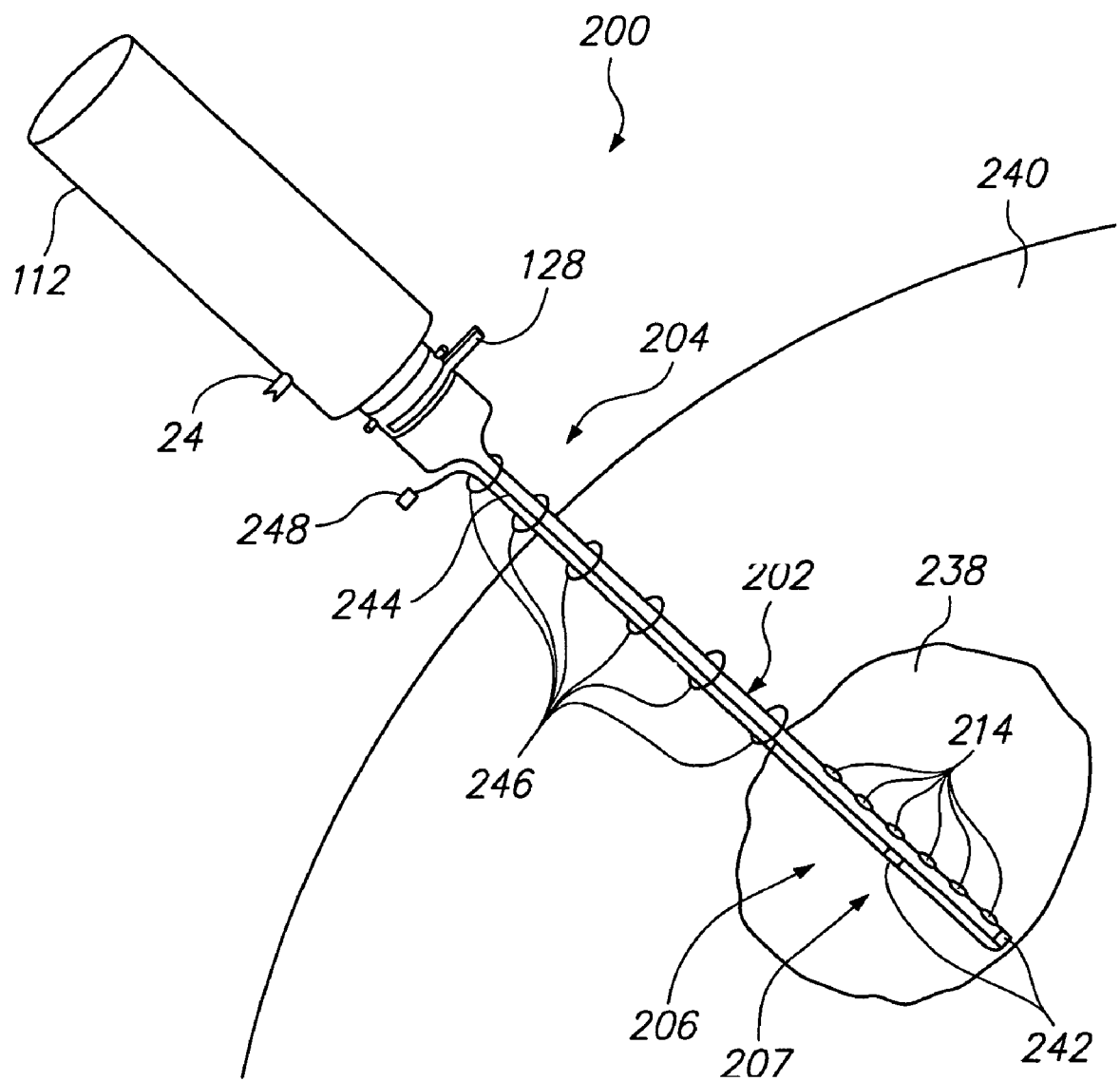
FIGS. 8A to 8C are perspective views of a method of using the delivery device of FIG. 7 to deliver medicament to an interstitial space within tissue.

Bending of the distal bendable section 207 of the elongated tube 201 can be effected by operation of the tensioning assembly 243. In particular, the tensioning assembly 243 comprises a tension cord 244 that is suitably mounted to the distal tip of the elongated tube 201 and a plurality of restraining rings 246 that are mounted along the tube 201. The tension cord 244 extends through the retraining rings 246, so that it is maintained in close contact with the tube 201. Thus, it can be appreciated that pulling the tension cord 244 causes the distal bendable section 207 to bend into an arc, as shown in FIG. 7. In contrast, relaxation of the tension cord 244 allows the distal bendable section 207 to assume a rectilinear geometry, as illustrated in FIG. 8A. The tensioning assembly 243 optionally comprises a grip 248 mounted to the proximal end of the tensioning cord 244, thereby allowing a user to more easily pull the tension cord 244. The grip 248 also allows the tension in the tension cord 244 to be maintained by locking the grip into a tension retainer 211 mounted on the handle 112.

Figure 8B:
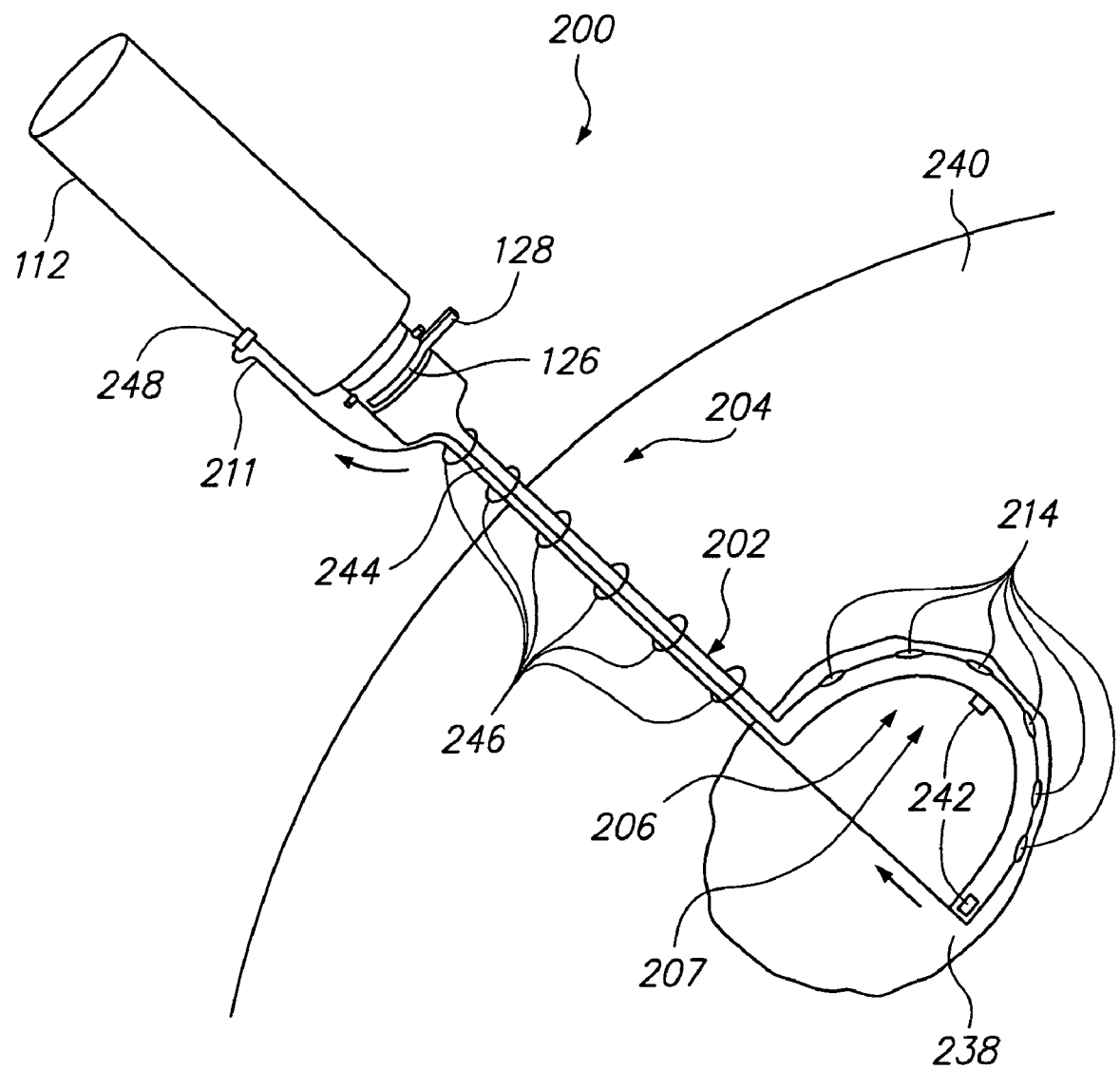
Figure 8C:
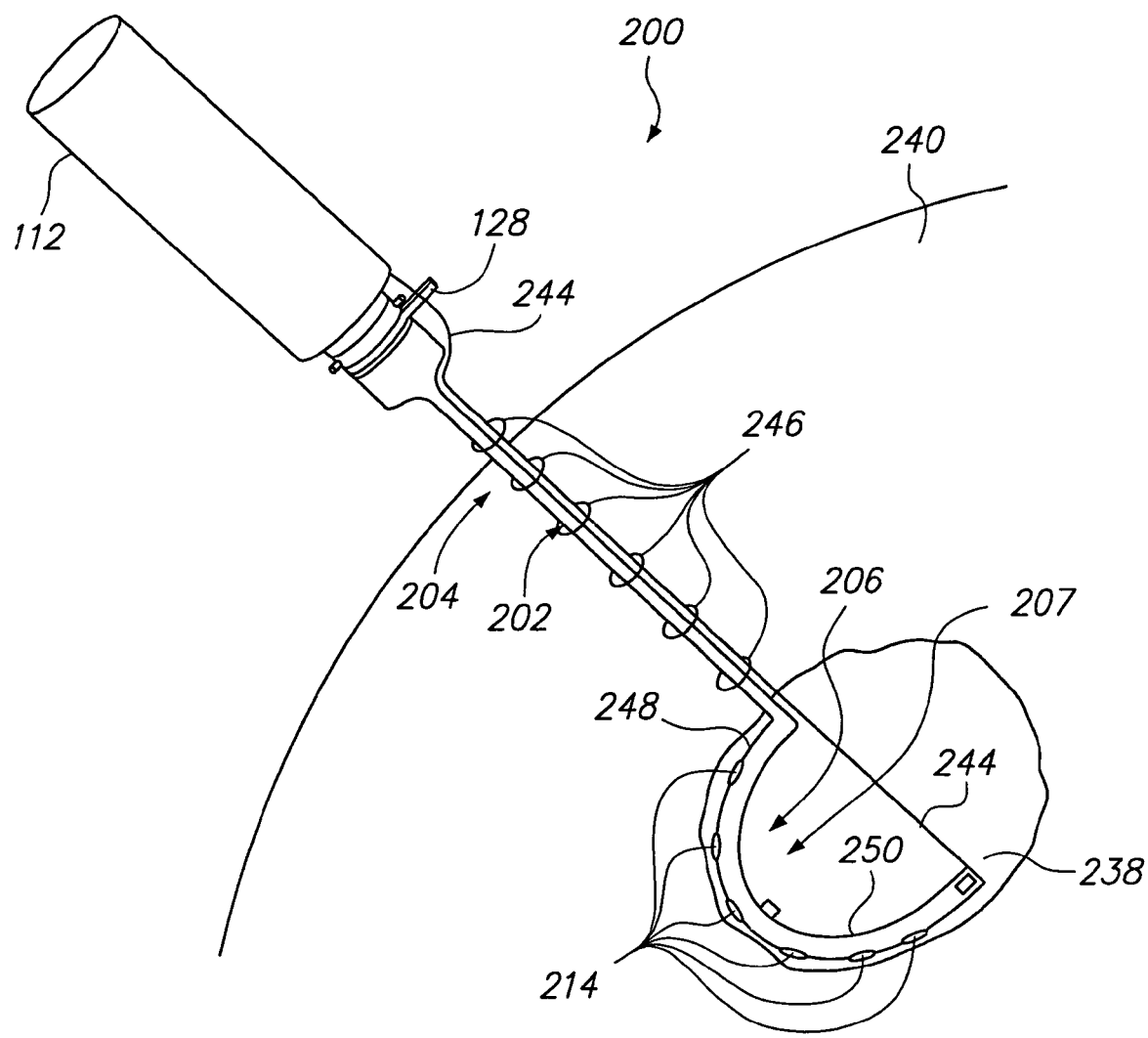

Referring to FIGS. 8A to 8C, the operation of the delivery device 200 in treating an interstitial space 238 from which a tumor (not shown) has been excised will now be described. One difference between the operation of this preferred embodiment of a delivery device 200 and the delivery device 100 previously described is the manner in which the ports 214 are brought into proximity to the margin of the interstitial space 238. Whereas the previously described delivery device 100 positions its ports 114 with an inflatable balloon 108 (see FIGS. 5A to 5C), the delivery device 200 uses the distal bendable section 207 and tension from a tension cord 244 to form an arc to position its ports 214.

As a result of the modified structure of the distal end 206 of the delivery member 202, the insertion and deployment of this delivery device 200 is also different from that of the previously described delivery device 100 (see FIGS. 5A to 5C). In particular, the delivery member 202 is inserted until the tip of the distal end 206 of the delivery member 202 reaches the distal end of the interstitial space 238 (FIG. 8A). The markers 242 can be used to more precisely position the delivery device 200.

To deploy the delivery device 200, i.e., to bring the ports 214 into proximity to the margin of the interstitial space 238, tension is applied to the tension cord 244 by pulling on the attached grip 248, thereby causing the bendable distal section 207 of the elongated tube 201 to bend into an arc (FIG. 8B). This change in geometry brings the ports 214 into proximity to the margin of the interstitial space 238. To maintain the tension and the geometry of the distal end 206, the grip 248 is locked into the tension retainer 211 on the handle 212.

The delivery device 200 is then rotated about its longitudinal axis to position the line of drug infusion ports 214 along the tissue to be treated, and the clutch 128 is manipulated to rotate the selector plate 126 to select, as described above, the lumen 222, and thus, the infusion port 214, through which drug will be delivered (FIG. 8C). Delivery of the medicament(s), including selection of different infusion ports 214 and any necessary flushing, can be accomplished in the same manner described above with respect to the delivery device 100. After the treatment of the overlying tissue 240 has been completed, the grip 248 is removed from the tension retainer 211 on the handle 212, releasing the tension on the bendable section 207. The resiliency of the bendable section 207 causes it to return to its rectilinear geometry, as shown in FIG. 8A. Then the delivery device 200, in its low profile state, can be removed from the overlying tissue 240 with minimal tissue trauma.

Figure 9:
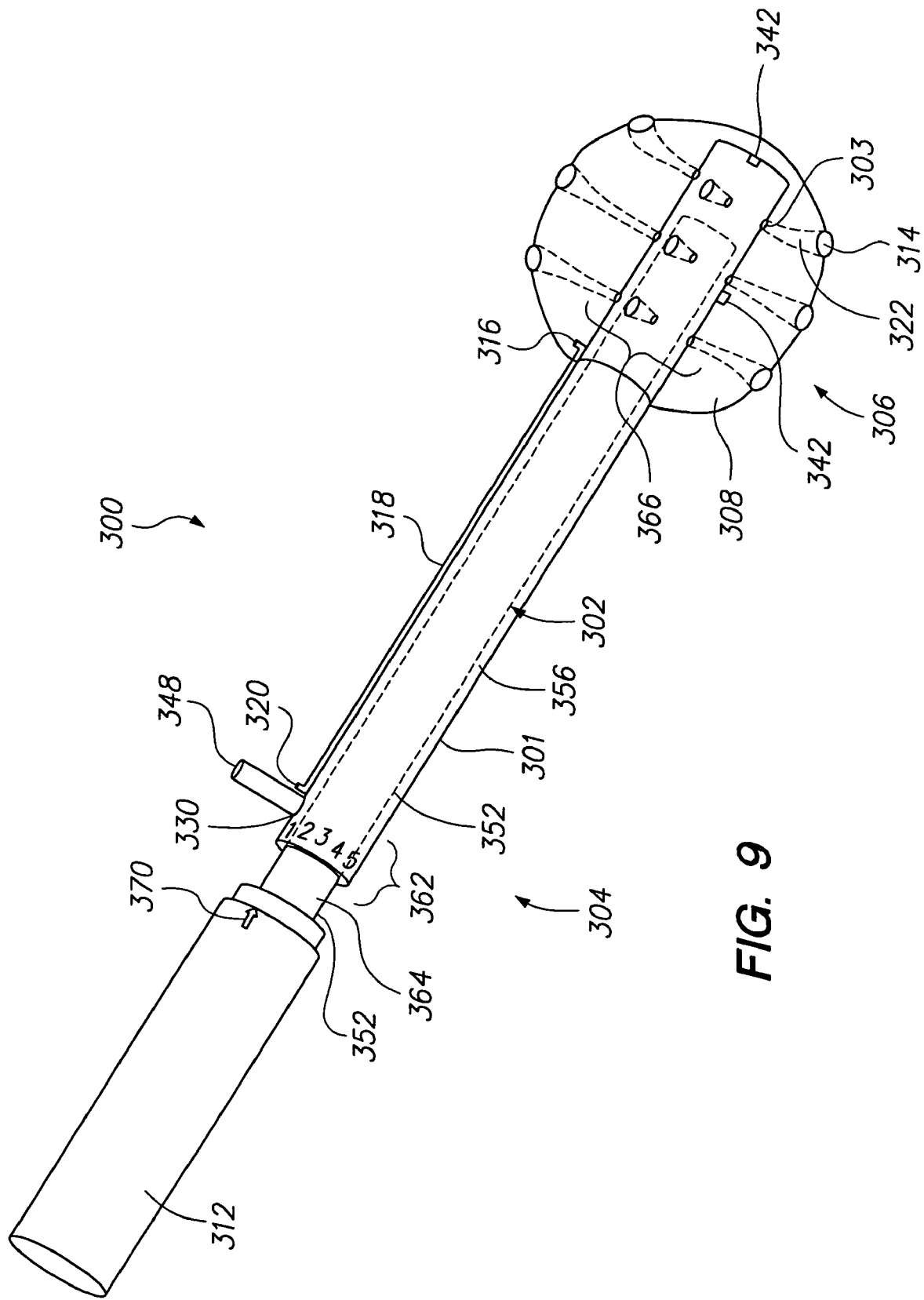
FIG. 9 is an exploded perspective view of a targeted drug delivery device constructed in accordance with still another preferred embodiment of the present invention.

Referring now to FIG. 9, another preferred embodiment of a targeted drug delivery device 300 will now be described. The delivery device 300 generally comprises an elongated delivery member 302 having a proximal end 304 and a distal end 306, an expandable body, and specifically a balloon 308, mounted along the distal end 306 of the delivery member 302 for delivery of drugs to a selected site, a drug port selector mechanism 352 mounted inside of the delivery member 302, and a handle 312 mounted to the selector mechanism 352.

Figure 12A:
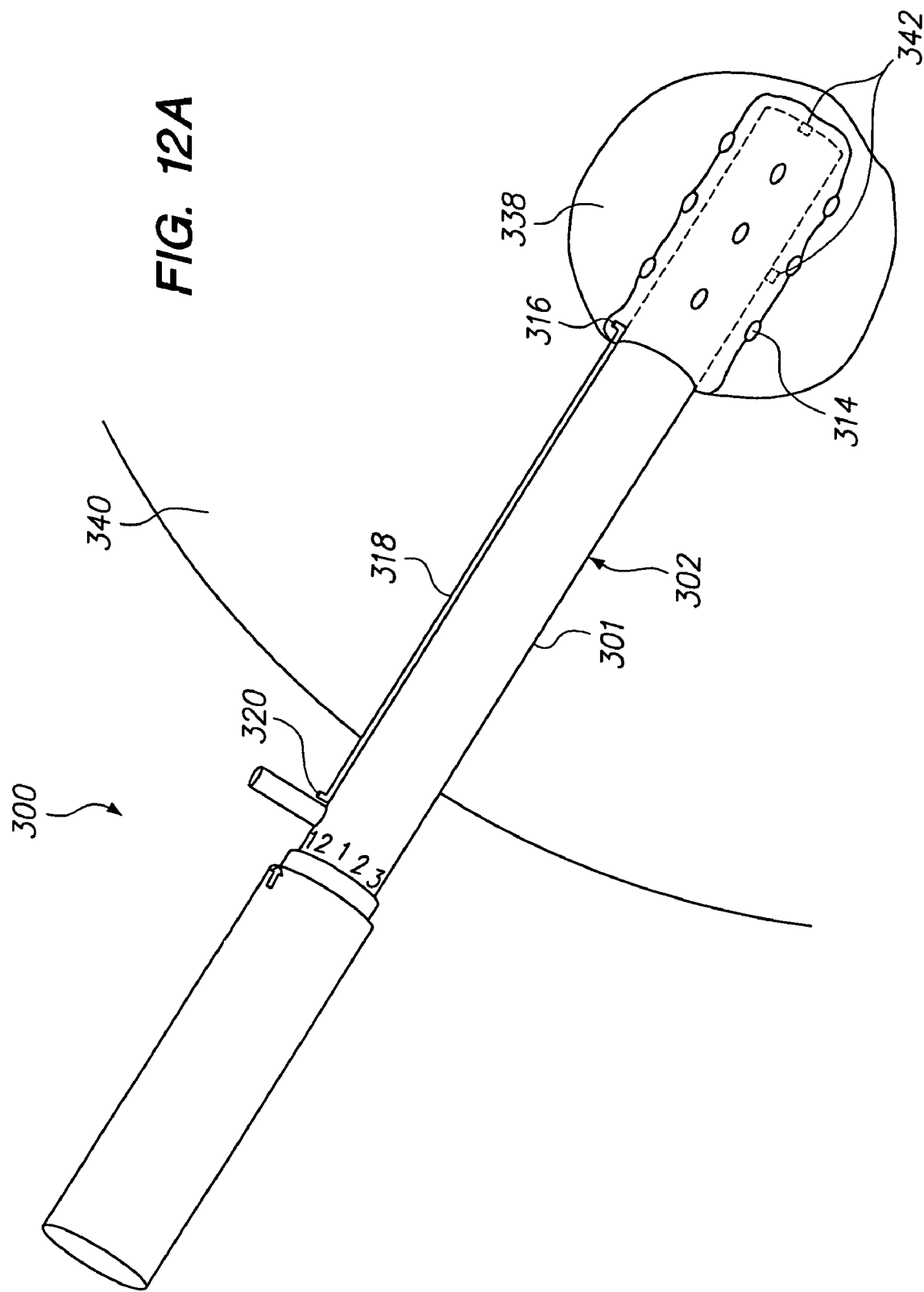

The delivery member 302 comprises an elongated tube 301 that may be formed using a standard extrusion process. In the preferred embodiment, the elongated tube 301 is rigid or semi-rigid, but may be flexible in some circumstances. The elongated tube 301 may be formed a biocompatible material, including plastic and other suitably rigid polymers. The elongated tube 301 has a series of holes 303 formed into its distal end 306 during extrusion. In the illustrated embodiment, the holes 303 are arranged in three rings 366, with four openings 303 for each ring 366. The delivery member 302 comprises an inflation duct 318 that extends along the elongated tube 301. In the illustrated embodiment, the inflation duct 318 takes the form of a separate tube of extruded polymer that is laminated to the outside of the elongated tube 301. Alternatively, the inflation duct 318 can take the form of a separate tube or an integrated lumen that extends within the interior of the elongated tube 301. The inflation duct 318 defines a proximal opening 320, which connects to a source of inflation medium, such as a syringe, and a distal opening 316, which terminates within the interior of the balloon 308. Fluid introduced into the proximal opening 320 of the inflation duct 318 will travel through the distal opening 316 of the inflation duct 318 and into the balloon 308, thereby placing the balloon 308 into its expanded geometry (as shown in FIG. 12B). Fluid removed from the proximal opening 320 of the inflation duct 318 will, in turn, remove the fluid from the balloon 308, thereby placing the balloon 308 into its collapsed geometry (shown in FIG. 12A).

The delivery member 302 further comprises a drug inlet port 330 at the proximal end 304 connected to a drug inlet duct 348. The drug inlet duct 348 is a rigid hollow tube extruded from a suitably rigid polymer and it is connect to the drug inlet port 330 by chemical bonding with an adhesive. The drug inlet duct 348 facilitates connection of the drug inlet port 320 to a source of drugs, such as a syringe.

The delivery member 302 further comprises a plurality of locating markers 342, which may be radio-opaque markers, signal transmitters, or signal receivers, mounted to the distal end of the elongated tube 301. Markers 342 interact with navigational systems (not shown) to more precisely position the delivery device 300. Also, a cutting edge (not shown) may be formed or separately attached to the distal end of the elongated tube 301. A skilled artisan will appreciate that a variety of cutting devices and catheter geometries and shapes would permit puncturing through overlying tissue.

The balloon 308 preferably comprises a highly compliant material that elastically expands upon pressurization. Because the balloon 308 elastically expands from the deflated state to the inflated state, the balloon 308 has a low profile in the deflated state and does not require balloon folding as with other non-compliant or semi-compliant balloon materials. Preferably, the balloon 308 is blow molded from a silicone. It should be noted, however, that non-compliant or semi-compliant balloon materials can be used without straying from the principles of the invention. The balloon 308 has a diameter of 15 mm to 20 mm.

The balloon 308 defines a plurality of drug infusion ports 314 on its surface. The ports 314 may either be formed into the balloon 308 during molding, or they are formed into the balloon 308 with a laser. Because the ports 314 are positioned on the balloon 308, the size of the ports 314 increases as the balloon 308 is inflated. The size of the ports 314 may be selected to allow the balloon 308 to control the pressure of the fluid to be introduced through the ports 314. The number of the ports 314 may be selected to adjust the precision with which a location on the balloon 308 will be selected. In this preferred embodiment, the ports 314 are equally spaced along four evenly distributed lines parallel to the longitudinal axis of the delivery member 302. The ports 314 may extend at an orthogonal angle through the wall of the balloon 308, or at a non-orthogonal to project the fluid more distally or more proximally as desired. Alternatively, protrusions (not shown) may be formed on the balloon 308 during blow molding and the ports 314 may be positioned on these protrusions. Protrusions will allow the balloon 308 to more easily grasp overlying tissue when the balloon 308 is inflated for more directed delivery of a drug.

The drug delivery device 300 further comprises drug delivery lumens 322, which connect the holes 303 on the elongated tube 301 with the ports 314 on the balloon 308. In the illustrated embodiment, the drug delivery lumens 322 are formed of separate tubes extruded from polymer. The holes 303 are connected to the proximal ends of the drug delivery lumens 322 by heat bonding or with an adhesive. Likewise, the ports 314 are connected to the distal ends of the drug delivery lumens 322 by heat bonding or with an adhesive.

In the illustrated embodiment, the balloon 308 is chemically bonded to the distal end of the elongated tube 301 with an adhesive, or the two elements can be heat bonded together. During bonding, the holes 303 in the elongated tube 301 should be sealed against the drug delivery lumens 322 so that the interior of the elongated tube 301 is not in fluid communication with the interior of the balloon 308.

The selector mechanism 352 comprises a cylindrical rod 364 and a plurality of stoppers 358 mounted on the distal end of the rod 364. In the illustrated embodiment, the stoppers 358 are arranged in three stopper rings 368, with eleven stoppers 358 per stopper ring 368, along the length of the distal end of the selector mechanism 352. (See FIGS. 10 and 11.) The stopper rings 368 are aligned with the hole rings 366, such that the stoppers 358 can be aligned with the holes 303, thereby closing them. As shown in FIG. 11, each stopper 358 is separated from the next by a rotational distance of 30 degrees. This construction results in one open space 360, i.e., a span of 30 degrees without any stopper 358, per ring 368. The spaces 360 in the three stopper rings 368 are rotationally displaced from each other by 30 degrees. When a space 360 is aligned with a hole 303, that hole 303 is open. Alternatively, the selector mechanism 352 may have three cams (not shown) in place of the three rings 368, where each cam has a space (spanning 30 degrees) in it. Although this example shows a selector mechanism 352 that closes all but one of the ports 314, other selector mechanisms may leave a plurality or all of the ports 314 open.

The elongated tube 301 and the selector mechanism 352 define between them an annular lumen 356, such that when a drug is introduced into the drug inlet duct 348, it travels through the annular lumen 356, out the open hole 303, through the connected drug delivery lumen 322, and out the connected drug infusion port 314.

In the illustrated embodiment, the rod 364 and stoppers 358 are formed of a single piece of material, such as a rigid polymer. Alternatively, the rod 364 and stoppers 358 may be discrete pieces, in which case, the stoppers 358 will be mounted to the distal end of the rod 358 using suitable means, such as chemical or heat bonding. Optionally, the stoppers 358 may be coated with a softer polymer to provide a better seal.

The handle 312 is rotatably mounted to the elongated tube 301 and gaskets (not shown) are used to make the connection substantially leak proof. This arrangement allows the handle 312 and the selector mechanism 352 attached thereto to rotate relative to the delivery member 302, while resisting leaks.

The handle 312 is connected to the selector mechanism 352 using, e.g., an adhesive or heat bonding. The handle 312 can be ergonomically designed for ease of operation of the delivery device 300. The elongated delivery member 302 comprises key information 362 and the handle 312 comprises an indicator 370, which interact to indicate the position of the selector mechanism 352 while it is obscured from view by the elongated tube 301.

Markers 342 are attached to the delivery member 302. Construction of the markers 342 and a cutting edge (not shown) is identical to the corresponding elements in previously described preferred embodiment 100.

Figure 10:
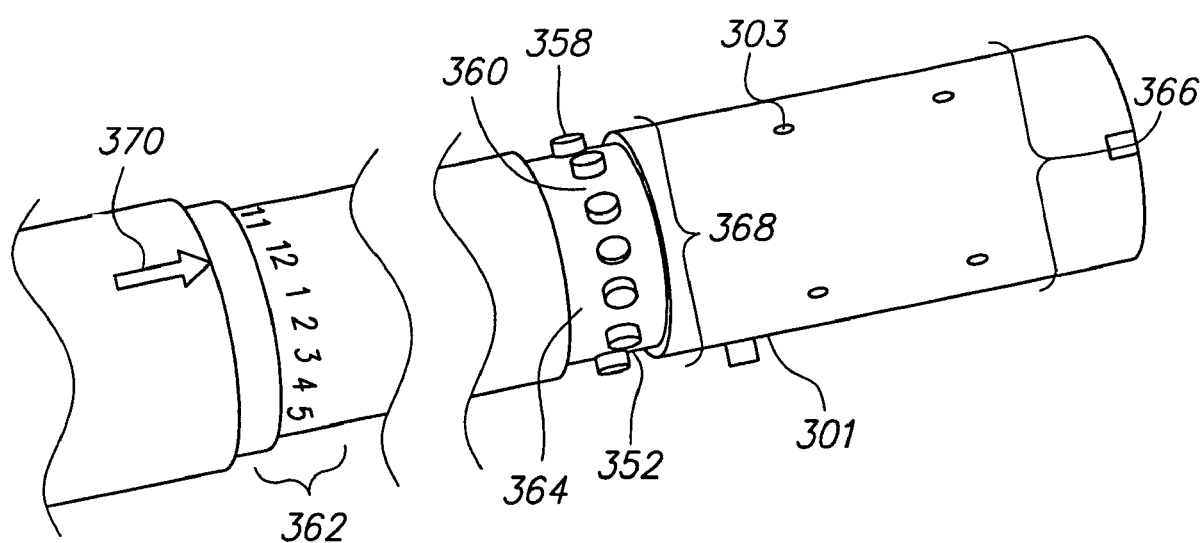
FIG. 10 is a cutaway perspective view of the delivery device of FIG. 9.
Figure 11:
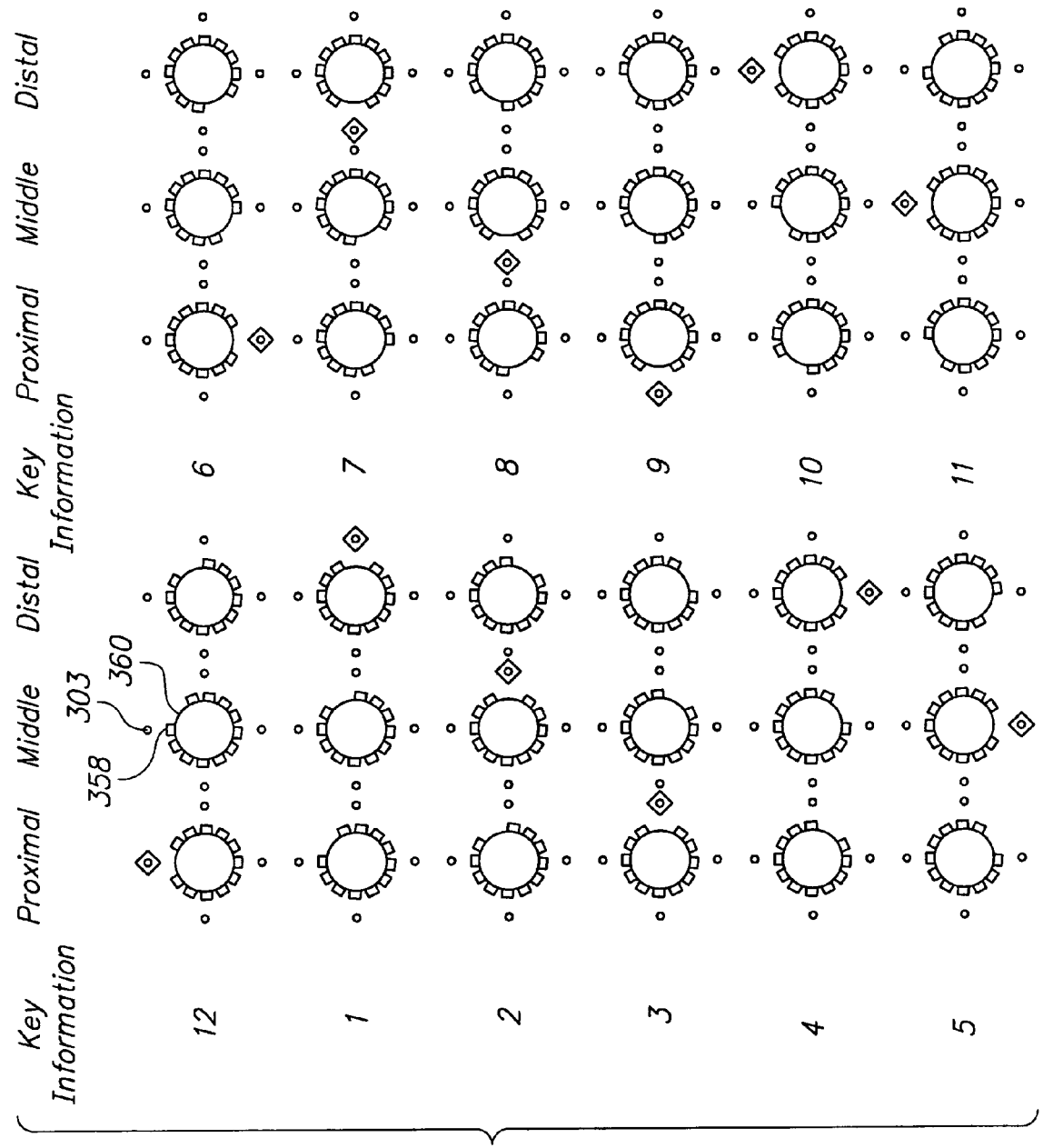
FIG. 11 are proximal axial views of the stoppers used in the delivery device of FIG. 9, showing different positions of the stoppers for opening and closing channel openings.

Referring to FIGS. 10 and 11, the operation of the selector mechanism 352, in determining the hole 303, and thus the corresponding drug infusion port 314 (see FIG. 9), through which fluid will be introduced is described. In FIGS. 10 and 11, the relationship between rotation of the selector mechanism 352 and the alignment of stoppers 358 and spaces 360 (shown in the cut-out section in FIG. 10) with holes 303 can be seen. When a stopper 358 on the selector mechanism 352 is positioned under a hole 303 in the elongated tube 301, the stopper 358 closes that hole 303. When a space 360 on the selector mechanism 352 is positioned under a hole 303 in the elongated tube 301, the hole 303 is open. It is evident that when the indicator 370 is aligned with the number 12 in the key information 362, the hole 303 at twelve o'clock (North) in the proximal most hole ring 366 is open, opening the attached drug delivery lumen 322 and the corresponding drug infusion port 314.

FIG. 11 shows schematically twelve positions of the selector mechanism 352 and the corresponding key information 362 and positions of the proximal, middle, and distal stopper rings 368 in relationship to the holes 303 in the elongated tube 301. In position 12, the hole 358 at twelve o'clock (North) on the proximal most hole ring 366 is the only one of the twelve holes 358 that is open (marked with a diamond). In fact, FIG. 11 shows that the arrangement of stoppers 358, spaces 360 and holes 303 in this embodiments only allows one hole 303 to be open in any of the twelve listed positions. Therefore, by orienting the selector mechanism 352 in one of the twelve positions pictured in FIG. 11, a user can determine which hole 303, which attached drug delivery channel 322, and ultimately, which drug infusion port 314 is open. The orientation of the selector mechanism 352 is changed by fixing the delivery member 302 and rotating the handle 312, which is connected to the selector mechanism 352.

As shown in FIG. 11, when the indicator 370 is oriented to the 1 o'clock position in the key information 362, the East hole 303 in the distal hole ring 366 is the only open hole 303. When the indicator 370 is oriented to the 2 o'clock position in the key information 362, the East hole 303 in the middle hole ring 366 is the only open hole 303. When the indicator 370 is oriented to the 3 o'clock position in the key information 362, the East hole 303 in the proximal hole ring 366 is the only open hole 303.

When the indicator 370 is oriented to the 4 o'clock position in the key information 362, the South hole 303 in the distal hole ring 366 is the only open hole 303. When the indicator 370 is oriented to the 5 o'clock position in the key information 362, the South hole 303 in the middle hole ring 366 is the only open hole 303. When the indicator 370 is oriented to the 6 o'clock position in the key information 362, the South hole 303 in the proximal hole ring 366 is the only open hole 303.

When the indicator 370 is oriented to the 7 o'clock position in the key information 362, the West hole 303 in the distal hole ring 366 is the only open hole 303. When the indicator 370 is oriented to the 8 o'clock position in the key information 362, the West hole 303 in the middle hole ring 366 is the only open hole 303. When the indicator 370 is oriented to the 9 o'clock position in the key information 362, the West hole 303 in the proximal hole ring 366 is the only open hole 303.

When the indicator 370 is oriented to the 10 o'clock position in the key information 362, the North hole 303 in the distal hole ring 366 is the only open hole 303. When the indicator 370 is oriented to the 11 o'clock position in the key information 362, the North hole 303 in the middle hole ring 366 is the only open hole 303.

Referring now to FIGS. 12A to 12C, the operation of the delivery device 300 in treating an interstitial space 338 from which a tumor (not shown) has been excised will now be described. First, the delivery device 300 is inserted through the overlying tissue 340 and into the interstitial space 338 until the distal tip of the delivery member 302 reaches the distal end of the interstitial space 338 (FIG. 12A). The markers 342 can be used to more precisely position the delivery device 300.

An inflation medium is then introduced into the inflation port 320, through the inflation duct 318, and into the balloon 308, thereby expanding the balloon 308 until all of its surfaces are juxtaposed to the interior margin of the interstitial space 338 (FIG. 12B). Inflation of the balloon 308 is identical to inflation of the previously described balloon 108.

The handle 312 is then rotated to rotate the selector mechanism 352 to select, as described above, the hole 303, the connected drug delivery lumen 322, and thus, the connected drug infusion port 314, through which drug will be delivered. The markers 342 can be used to more precisely identify the position of the delivery device 300.

Once the region on the margin of the interstitial space has been selected for treatment, a medicament is delivered into the drug inlet port 330 via the drug inlet duct 348. The medicament will travel into the annular lumen 356, through the open hole 303, into the open drug delivery lumen 322, and out the corresponding drug infusion port 314. The proximity of the selected infusion port 314 to the selected region on the margin of the interstitial space 338 will result in forced convection delivery of the medicament to the tissue 340.

The delivery device 300 can optionally be flushed with a biologically inactive liquid, such as saline or Ringer's solution, to ensure that all of the medicament has been delivered to the region. If flushing the interstitial space 338 with additional liquid is not desirable, the excess volume represented by the annular lumen 356 and the drug delivery lumen 322 can be taken into account when calculating the amount of the medicament to be used.

If a second region on the margin of the interstitial space 338 is to be treated, the handle 312 can be rotated as described above to selected the drug infusion port 314 closest to the second region (see FIG. 12C). If the second region is to be treated with the same medicament as the first region, the medicament is again delivered through the drug inlet port 330. Additional regions can be treated with the same medicament in the same manner.

If the second or subsequent regions are to be treated with a different medicament, however, the medical device 300 is preferably first flushed as described above to remove any traces of the first medicament from the medical device 300.

Once all selected points on the margin of the interstitial space 338 have been treated, the balloon 308 can be deflated by removing the inflation medium from the proximal opening 320, thereby placing the balloon 308 in its deflated state. The delivery device 300, in its low profile state, can then be removed from the tissue 340.

Referring now to FIG. 13, another preferred embodiment of a targeted drug delivery device 400 will now be described. The delivery device 400 generally comprises an elongated delivery member 402 having a proximal end 404 and a distal end 406, a plurality of bendable hollow drug delivery arms 472 connected to the distal end 406 of the delivery member 402, an arm restraining sheath 474 slidably mounted along the delivery member 402, a selector mechanism 452 mounted inside of the delivery member 402, and the previously described handle 312.

Like the previously described delivery member 302, the delivery member 402 comprises an elongated tube 401 and an annular lumen 456 that extends through the tube 401 between the proximal 406 and distal ends 404. The distal end of the annular lumen 456, however, terminates in holes 403 formed in the distal end 406 of the elongated tube 401. The holes 403 are connect to bendable hollow drug delivery arms 472, with each of the hollow drug delivery arms 472 is in fluid connection with a unique hole 403 in the elongated tube 401 (see FIG. 14). Each delivery arm 472 defines a drug infusion port 414 along its length. Four of the arms 472 define drug infusion ports 414 in their proximal portion. Another four of the arms 472 define drug infusion ports 414 in their middle portion. The last four of the arms 472 define drug infusion ports 414 in their distal portion.

Like the elongated tube 301 described above, the elongated tube 401 is rigid or semi-rigid, but may be flexible in some circumstances. The elongated tube 401 may be formed from a biocompatible material, including plastic and other suitably rigid polymers. The drug delivery arms 472, on the other hand, are composed of an easily flexible deformable, yet resilient, material, such as nickel titanium or polyimide. The flexibility of the drug delivery arms 472 allows them to bend into a low profile shape when they are restrained by the sheath 474 (see FIG. 16A). The resiliency of the drug delivery arms 472 allow them to bend back into a spherical geometry once the tension is removed. The delivery member can carry markers 442 to provide navigational ability.

Figure 16A:
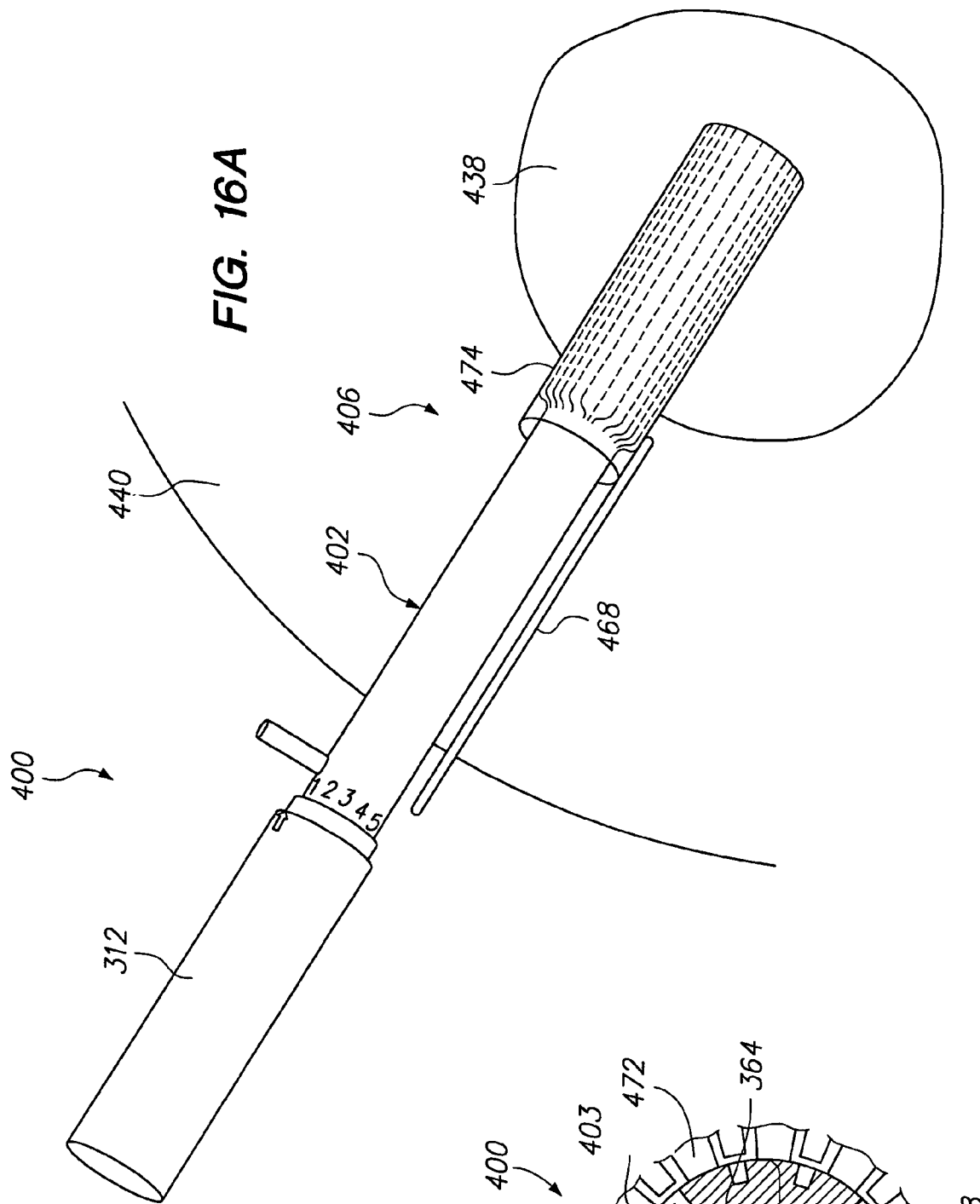
FIGS. 16A and 16B are perspective views of a method of using the delivery device of FIG. 13 to deliver medicament to an interstitial space within tissue.
Figure 16B:
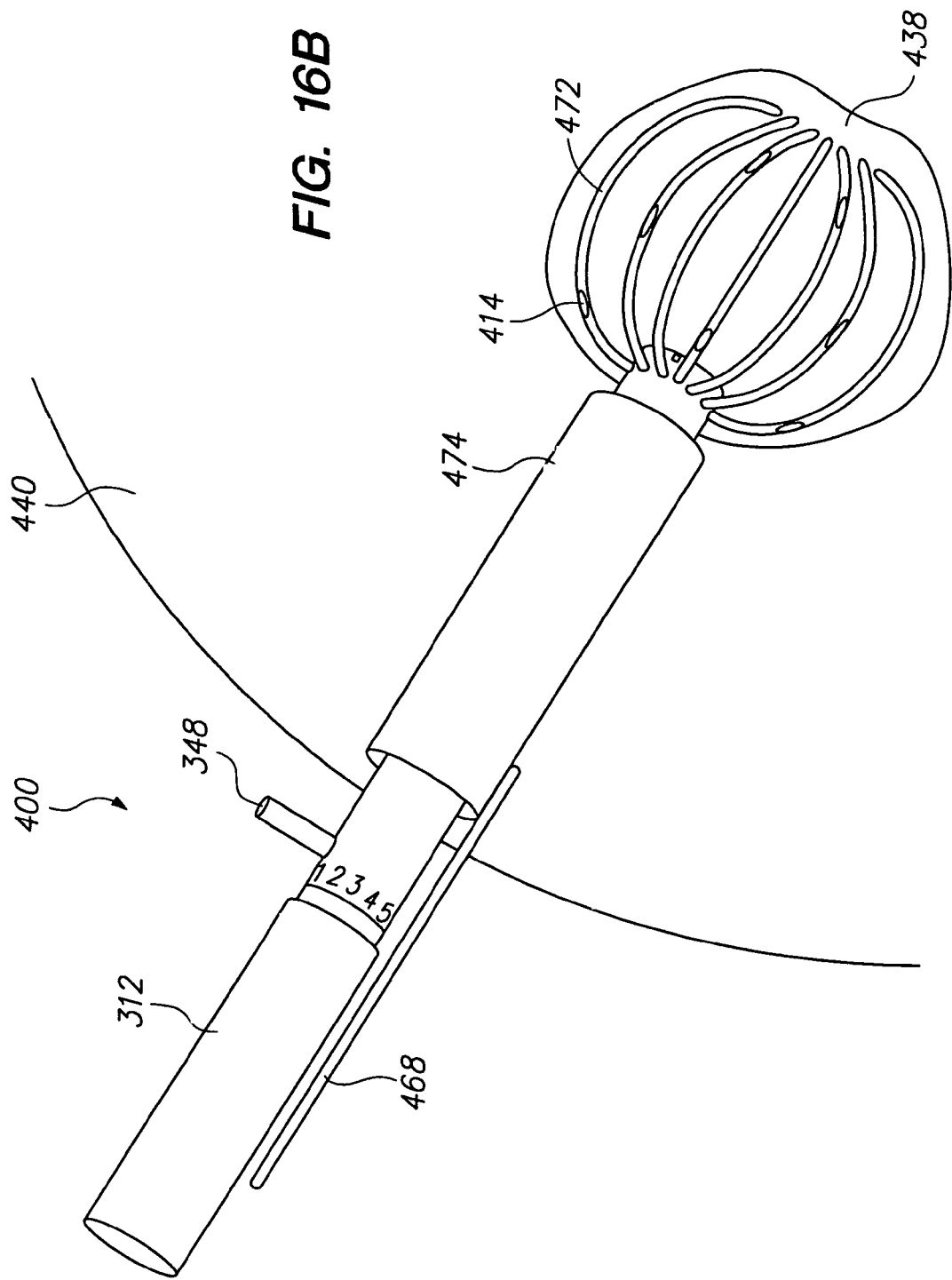

The arm restraining sheath 474 is mounted to the delivery member 402 so that it can slide along the longitudinal axis of the delivery member 402. A sheath manipulating bar 476 is connected to the proximal end of the sheath 474, so that the bar 476 can be used to slide the sheath 474 along the delivery member 402. Bending of the drug delivery arms 472 can be effected by operation of a sheath manipulating bar 476. In particular, the bar 476 is connected to the arm restraining sheath 474, which is slidably mounted to the elongated tube 401. Thus, it can be appreciated that pushing the bar 476 in the distal direction causes the sheath 474 to slide over the drug delivery arms 472 and to bend the arms 472 into a low profile configuration, as shown in FIG. 16A. In contrast, pulling the bar 476 in the proximal direction allows the drug delivery arms 472 to assume a spherical geometry, as illustrated in FIG. 16B.

Like the previously described selector mechanism 352, the selector mechanism 452 comprises a cylindrical rod 364. The selector mechanism 452 of this embodiment, however, only has one stopper ring 368 (see FIG. 15), comprising eleven stoppers 358 and one space 360, located at the distal end of the cylindrical rod 364. The stopper ring 368 in this drug delivery device 400 is identical to the three stopper rings 368 in the previously described drug delivery device 300. Alternatively, the selector mechanism 452 may have a cam (not shown) in place of the stopper ring 368, where the cam has a space (spanning 30 degrees) in it. With the exception of the presence of one ring of stoppers 358 instead of three rings, the selector mechanism 452 is structurally identical to the previously described selector mechanism 352.

The elongated tube 401 and the selector mechanism 452 define between them an annular lumen 456, such that when a drug is introduced into the drug inlet duct 348, it travels through the annular lumen 456, out the open gap 403, through the connected drug delivery arm 472, and out the connected drug infusion port 414.

Although this preferred embodiment shows a selector mechanism 452 that closes all but one of the arms 472, other selector mechanisms may leave a plurality or all of the arms 472 open. Although this preferred embodiment shows that each arm 472 only defines one port 414, other embodiments may have arms with more than one port.

Figure 15:
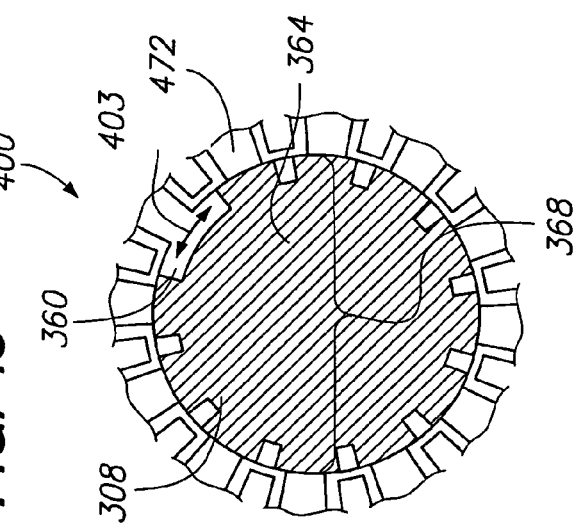
FIG. 15 is a cross-sectional view of the delivery device of FIG. 13 along line 15-15 in FIG. 13.

FIG. 15 shows the selector mechanism 452 closing all of the holes 403 on the elongated tube 401 except for the hole 403 at one o'clock. It can be appreciated that rotating the selector mechanism 452 within the elongated tube 401, as described above with respect to delivery device 300, will, in turn, open each of the holes 403 on the elongated tube 401.

Referring to FIGS. 16A and 16B, the operation of the delivery device 400 in treating an interstitial space 438 from which a tumor (not shown) has been excised will now be described. One difference between the operation of this preferred embodiment of a delivery device 400 and the delivery device 300 previously described is the manner in which the ports 414 are brought into proximity to the margin of the interstitial space 438. Whereas the previously described delivery device 300 positions its ports 314 with an inflatable balloon 308 (see FIGS. 12A to 12C), the delivery device 400 uses the bendable hollow drug delivery arms 472 and their resiliency to form a sphere to position its ports 414.

As a result of the modified structure of the distal end 406 of the delivery member 402, the insertion and deployment of this delivery device 400 is also different from that of the previously described delivery device 300 (see FIGS. 12A to 12C). In particular, the delivery member 402 is inserted until the tip of the distal end 406 of the delivery member 402 reaches the distal end of the interstitial space 438 (FIG. 16A). The markers 442 (see FIG. 13) can be used to more precisely position the delivery device 400.

To deploy the delivery device 400, i.e., to bring the ports 414 into proximity to the margin of the interstitial space 438, tension is released from the drug delivery arms 472 by removing the sheath 474 from the arms 472, thereby allowing the resilient arms 472 to form a sphere (FIG. 16B). This change in geometry brings the ports 414 into proximity to the margin of the interstitial space 438.

The handle 312 is manipulated to rotate the selector mechanism 452 (see FIG. 13) to select, as described above, the drug delivery arm 472, and thus, the drug infusion port 414, through which drug will be delivered. Delivery of the medicament(s), including selection of different infusion ports 414 and any necessary flushing, can be accomplished in the same manner described above with respect to the delivery device 300. After the treatment of the overlying tissue 440 has been completed, the sheath 474 is pushed over the drug delivery arms 472 as described above. The flexibility of the drug delivery arms 472 allows them to bend to a low profile geometry, as shown in FIG. 16A. Then the delivery device 400, in its low profile state, can be removed from the overlying tissue 440 with minimal tissue trauma.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical device, comprising:
    an elongated member having a proximal end and a distal end;
    a plurality of infusion ports associated with the distal end of the member;
    a plurality of fluid delivery channels in fluid communication with the respective infusion ports;
    an introduction port configured to be in selective fluid communication with each of the plurality of fluid delivery channels; and
    a selector mechanism configured for selectively placing the introduction port into fluid communication with a respective infusion port via a respective fluid delivery channel, the selector mechanism comprising:
        a rotatable selector plate having at least one through-hole that can be selectively aligned with a proximal opening of a respective fluid delivery channel, and
        a manifold positioned between the introducer port and the selector plate, the manifold having a cavity in fluid communication between the introduction port and the at least one selector plate hole.

2. The device of claim 1, wherein the elongated member is axially rigid.

3. The device of claim 1, wherein the plurality of ports is formed in the distal end of the elongated member.

4. The device of claim 3, wherein the elongated member comprises a bendable distal section, the device further comprising an actuator configured for bending the distal end of the elongated member into an arc.

5. The device of claim 4, wherein the actuator comprises a tension cord attached to the distal end of the elongated member.

6. The device of claim 1, further comprising a radially expandable body surrounding the distal end of the member, wherein the plurality of ports is disposed on the radially expandable body.

7. The device of claim 6, wherein the expandable body comprises a balloon, and the device further comprises an inflation duct extending along the member in fluid communication with the interior of the balloon.

8. The device of claim 6, wherein the expandable body comprises a plurality of resilient arms that radially bend outward in the absence of a radially compressive force.

9. The device of claim 8, further comprising a sheath axially slidable along the elongated member and configured for applying a radially compressive force to the plurality of arms.

10. The device of claim 1, wherein the channels have proximal openings that terminate at the proximal end of the member.

11. The device of claim 1, wherein the channels have distal openings that terminate at the distal end of the member.

12. The device of claim 1, wherein the proximal ends of the channels are axially disposed.

13. The device of claim 1, further comprising a flush port in fluid communication with the manifold cavity.

14. The device of claim 1, wherein proximal ends of the channels are radially disposed, and the selector mechanism comprises a rod extending through the member and at least one annular arrangement having a gap that can be aligned with a proximal opening of a channel.

15. The device of claim 14, wherein the annular arrangement comprises a plurality of radially extending, evenly distributed, stops, and the gap represents a missing stop.

16. The device of claim 14, wherein the annular arrangement comprises a cam, and the gap is formed in the cam.

17. The device of claim 14, further comprising an annular lumen formed between the rod and the member, wherein the annular lumen is in fluid communication between the introduction port and the channels.

18. The device of claim 1, the selector mechanism placeable at a first position wherein the introduction port is in fluid communication with a first one of the infusion ports, and at a second position wherein the introduction port is in fluid communication with a second one of the infusion ports, wherein when the selector mechanism is at the first position, the introduction port is not in fluid communication with the second one of the infusion ports, and wherein when the selector mechanism is at the second position, the introduction port is not in fluid communication with the first one of the infusion ports.

19. The device of claim 1, further comprising a fluid source that is in fluid communication with the introduction port.

20. The device of claim 1, the selector mechanism placeable at a first position wherein the introduction port is in fluid communication with a first one of the infusion ports, and at a second position wherein the introduction port is in fluid communication with a second one of the infusion ports, wherein when the selector mechanism is at the first position, the introduction port is in fluid communication with the first one of the infusion ports, and not in fluid communication with any remaining ones of the infusion ports.

* * * * *